US012612459B2

(12) United States Patent
Hakim et al.

(10) Patent No.: US 12,612,459 B2
(45) Date of Patent: *Apr. 28, 2026

(54) METHODS OF IDENTIFYING AGENTS THAT BLOCK MCD28 CLEAVAGE BY MMPS

(71) Applicant: BIOND BIOLOGICS LTD., Misgav (IL)

(72) Inventors: Motti Hakim, Kibbutz Gazit (IL); Anna Fridman-Dror, Kibbutz Dalia (IL); Ilana Mandel, Manof (IL); Tehila Ben-Moshe, Tel Aviv (IL); Yair Sapir, Manof (IL); Avidor Shulman, Rakefet (IL)

(73) Assignee: BIOND BIOLOGICS LTD., Misgav (IL)

( * ) Notice: Subject to any disclaimer, the term of this patent is extended or adjusted under 35 U.S.C. 154(b) by 828 days.

This patent is subject to a terminal disclaimer.

(21) Appl. No.: 17/781,902

(22) PCT Filed: Dec. 2, 2020

(86) PCT No.: PCT/IL2020/051243
§ 371 (c)(1),
(2) Date: Jun. 2, 2022

(87) PCT Pub. No.: WO2021/111441
PCT Pub. Date: Jun. 10, 2021

(65) Prior Publication Data
US 2023/0041599 A1     Feb. 9, 2023

Related U.S. Application Data

(60) Provisional application No. 62/954,802, filed on Dec. 30, 2019, provisional application No. 62/942,240, filed on Dec. 2, 2019.

(30) Foreign Application Priority Data

Mar. 12, 2020     (WO) .................. PCT/IL2020/050297

(51) Int. Cl.
| | |
|---|---|
| *C07K 16/28* | (2006.01) |
| *A61K 31/18* | (2006.01) |
| *A61K 31/54* | (2006.01) |
| *A61K 35/15* | (2015.01) |
| *A61K 35/17* | (2015.01) |
| *A61K 39/00* | (2006.01) |
| *A61K 39/395* | (2006.01) |
| *A61P 35/00* | (2006.01) |
| *A61P 37/02* | (2006.01) |
| *G01N 33/574* | (2006.01) |

(52) U.S. Cl.
CPC .......... *C07K 16/2818* (2013.01); *A61K 31/18* (2013.01); *A61K 31/54* (2013.01); *A61K 35/15* (2013.01); *A61K 35/17* (2013.01); *A61K 39/0011* (2013.01); *A61K 39/3955* (2013.01); *A61P 35/00* (2018.01); *A61P 37/02* (2018.01);

*G01N 33/57492* (2013.01); *C07K 2317/22* (2013.01); *C07K 2317/34* (2013.01); *C07K 2317/569* (2013.01); *C07K 2317/76* (2013.01)

(58) Field of Classification Search
None
See application file for complete search history.

(56) References Cited

U.S. PATENT DOCUMENTS

2008/0038273 A1     2/2008   Soulillou et al.

FOREIGN PATENT DOCUMENTS

| | | | |
|---|---|---|---|
| CN | 100509849 C | 7/2009 | |
| EP | 1378520 A1 | 1/2004 | |
| JP | 2002541096 A | 12/2002 | |
| JP | 2010195797 A | 9/2010 | |
| WO | 2002047721 A1 | 6/2002 | |
| WO | 2004096139 A2 | 11/2004 | |
| WO | 2010009391 A1 | 1/2010 | |
| WO | 2016054218 A1 | 4/2016 | |
| WO | WO-2019175885 A1 * | 9/2019 | .............. A61P 35/00 |
| WO | WO-2020183473 A1 * | 9/2020 | .............. A61P 35/00 |

OTHER PUBLICATIONS

Li et al (Cellular & Molecular Immunology, 2010, 7:133-152).*
Mary et al (mAbs, 2013, 5:1, 47-55).*
Hebbar et al (Clinical Experimental Immunology, 2004, 136:388-392).*
Winer et al., "Matrix Metalloproteinase Inhibitors in Cancer Therapy: Turning Past Failures into Future Successes" Molecular Cancer Therapeutics, vol. 17, No. 6, Jun. 1, 2018, pp. 1147-1155. doi: 10.1158/1535-7163. MCT-17-0646. Epub May 7, 2018. PMID: 29735645; PMCID: PMC5984693.
Motti Hakim, "Abstract 2846A: CD28 shedding is a novel immune-regulatory mechanism found in cancer patients which directly inhibits anti PD-1 effect" Cancer Research, 80 (16_Supplement): 2846A. American Association for Cancer Research, Aug. 2020. https://doi.org/10.1158/1538-7 445.AM2020-2846A.
Lucas Ferrari De Andrade et al., "Antibody-mediated inhibition of MICA and MICB shedding promotes NK cell-driven tumor immunity" Science, vol. 359, No. 6383, Mar. 30, 2018, pp. 1537-1542. doi: 10.1126/science.aa00505. PMID: 29599246; PMCID: PMC6626532.

(Continued)

*Primary Examiner* — Laura B Goddard
(74) *Attorney, Agent, or Firm* — The Roy Gross Law Firm, LLC; Roy D. Gross

(57) ABSTRACT

Methods of decreasing shedding of CD28, decreasing soluble CD28 levels, treating cancer and improving immunotherapies comprising inhibiting matrix metalloproteases are provided. Methods of producing agents for performance of the methods of the invention are also provided.

7 Claims, 23 Drawing Sheets

Specification includes a Sequence Listing.

(56)         References Cited

OTHER PUBLICATIONS

Anderson H. Webb et al., "Inhibition of MMP-2 and MMP-9 decreases cellular migration, and angiogenesis in in vitro models of retinoblastoma" BMC Cancer, 17:434, 2017, 11 pages. doi: 10.1186/s12885-017-3418-y. PMID: 28633655; PMCID: PMC5477686.

Alice Meides et al., "Effects of selective MMP-13 inhibition in squamous cell carcinoma depend on estrogen" International Journal of Cancer, 135, pp. 2749-2759, 2014. doi: 10.1002/ijc.28866. Epub Aug. 7, 2014. PMID: 24676718.

Magistrelli G, Jeannin P, Elson G, Gauchat JF, Nguyen TN, Bonnefoy JY, Delneste Y. Identification of three alternatively spliced variants of human CD28 mRNA. Biochem Biophys Res Commun. May 27, 1999;259(1):34-7. doi: 10.1006/bbrc.1999.0725. PMID: 10334911.

Murray ME, Gavile CM, Nair JR, Koorella C, Carlson LM, Buac D, Utley A, Chesi M, Bergsagel PL, Boise LH, Lee KP. CD28-mediated pro-survival signaling induces chemotherapeutic resistance in multiple myeloma. Blood. Jun. 12, 2014;123(24):3770-9. doi: 10.1182/blood-2013-10-530964. Epub Apr. 29, 2014. PMID: 24782505; PMCID: PMC4055924.

Danquah W, Meyer-Schwesinger C, Rissiek B, Pinto C, Serracant-Prat A, Amadi M, Iacenda D, Knop JH, Hammel A, Bergmann P, Schwarz N, Assunção J, Rotthier W, Haag F, Tolosa E, Bannas P, Boué-Grabot E, Magnus T, Laeremans T, Stortelers C, Koch-Nolte F. Nanobodies that block gating of the P2X7 ion channel ameliorate inflammation. Sci Transl Med. Nov. 23, 2016;8(366):366ra162. doi: 10.1126/scitranslmed.aaf8463. PMID: 27881823.

Hebbar M, Jeannin P, Magistrelli G, Hatron PY, Hachulla E, Devulder B, Bonnefoy JY, Delneste Y. Detection of circulating soluble CD28 in patients with systemic lupus erythematosus, primary Sjögren's syndrome and systemic sclerosis. Clin Exp Immunol. May 2004;136(2):388-92. doi: 10.1111/j. 1365-2249.2004.02427.x. PMID: 15086406; PMCID: PMC1809021.

Sun Z, Yi L, Tao H, Huang J, Jin Z, Xiao Y, Feng C, Sun J. Enhancement of soluble CD28 levels in the serum of Graves' disease. Cent Eur J Immunol. 2014;39(2):216-22. doi: 10.5114/ceji. 2014.43726. Epub Jun. 27, 2014. PMID: 26155127; PMCID: PMC4440026.

Wong CK, Lit LC, Tam LS, Li EK, Lam CW. Aberrant production of soluble costimulatory molecules CTLA-4, CD28, CD80 and CD86 in patients with systemic lupus erythematosus. Rheumatology (Oxford). Aug. 2005;44(8):989-94. doi: 10.1093/rheumatology/keh663. Epub May 3, 2005. PMID: 15870153.

Hamzaoui K, Hamzaoui A, Bouajina L, Houman H. Circulating soluble CD28 in patients with Behçet's disease: relationship to clinical manifestations. Clin Exp Rheumatol. Jul.-Aug. 2005;23(4 Suppl 38):S49-52. PMID: 16273764.

Daniel et al., Costimulation With Agonistic ANTI-CD28 Antibodies Prevents T Cell Apoptosis and is Required for Efficient Immunotherapy With CD3x19 Bispecific Antibodies in B Cell Lymphoma. Free communications and posters, Article 97, S42, 1997.

Hedemann N, Rogmans C, Sebens S, Wesch D, Reichert M, Schmidt-Arras D, Oberg HH, Pecks U, van Mackelenbergh M, Weimer J, Arnold N, Maass N, Bauerschlag DO. ADAM17 inhibition enhances platinum efficiency in ovarian cancer. Oncotarget. Mar. 23, 2018;9(22):16043-16058. doi: 10.18632/oncotarget. 24682. PMID: 29662625; PMCID: PMC5882316.

Huang Y, Benaich N, Tape C, Kwok HF, Murphy G. Targeting the sheddase activity of ADAM17 by an anti-ADAM17 antibody D1(A12) inhibits head and neck squamous cell carcinoma cell proliferation and motility via blockage of bradykinin induced HERs transactivation. Int J Biol Sci. Jun. 21, 2014;10(7):702-14. doi: 10.7150/ijbs. 9326. PMID: 25013379; PMCID: PMC4081605.

Isitmangil G, Gurleyik G, Aker FV, Coskun C, Kucukhuseyin O, Arikan S, Turan S, Talu CK, Dogan MB, Farooqi AA, Yaylim I. Association of CTLA4 and CD28 Gene Variants and Circulating Levels of Their Proteins in Patients with Breast Cancer. In Vivo. Jul.-Aug. 2016;30(4):485-93. PMID: 27381613.

Wang H, Wang K, Zhong X, Dai Y, Wu A, Li Y, Hu X. Plasma sCD28, sCTLA-4 levels in neuromyelitis optica and multiple sclerosis during relapse. J Neuroimmunol. Feb. 29, 2012;243(1-2):52-5. doi: 10.1016/j.jneuroim.2011.11.010. Epub Dec. 15, 2011. PMID: 22177277.

Igawa T, Haraya K, Hattori K. Sweeping antibody as a novel therapeutic antibody modality capable of eliminating soluble antigens from circulation. Immunol Rev. Mar. 2016;270(1):132-51. doi: 10.1111/imr.12392. PMID: 26864109.

Ip WK, Wong CK, Leung TF, Lam CW. Plasma concentrations of soluble CTLA-4, CD28, CD80 and CD86 costimulatory molecules reflect disease severity of acute asthma in children. Pediatr Pulmonol. Jul. 2006;41(7):674-82. doi: 10.1002/ppul.20432. PMID: 16703581.

Schröter C, Günther R, Rhiel L, Becker S, Toleikis L, Doerner A, Becker J, Schonemann A, Nasu D, Neuteboom B, Kolmar H, Hock B. A generic approach to engineer antibody pH-switches using combinatorial histidine scanning libraries and yeast display. MAbs. 2015;7(1):138-51. doi: 10.4161/19420862.2014.985993. PMID: 25523975; PMCID: PMC4622719.

Yang D, Giragossian C, Castellano S, Lasaro M, Xiao H, Saraf H, Hess Kenny C, Rybina I, Huang ZF, Ahlberg J, Bigwarfe T, Myzithras M, Waltz E, Roberts S, Kroe-Barrett R, Singh S. Maximizing in vivo target clearance by design of pH-dependent target binding antibodies with altered affinity to FcRn. MAbs. Oct. 2017;9(7):1105-1117. doi: 10.1080/19420862.2017.1359455. Epub Aug. 8, 2017. PMID: 28786732; PMCID: PMC5627591.

Kamphorst AO, Wieland A, Nasti T, Yang S, Zhang R, Barber DL, Konieczny BT, Daugherty CZ, Koenig L, Yu K, Sica GL, Sharpe AH, Freeman GJ, Blazar BR, Turka LA, Owonikoko TK, Pillai RN, Ramalingam SS, Araki K, Ahmed R. Rescue of exhausted CD8 T cells by PD-1-targeted therapies is CD28-dependent. Science. Mar. 31, 2017;355 (6332): 1423-1427. doi: 10.1126/science.aaf0683. Epub Mar. 9, 2017. PMID: 28280249; PMCID: PMC5595217.

Hui E, Cheung J, Zhu J, Su X, Taylor MJ, Wallweber HA, Sasmal DK, Huang J, Kim JM, Mellman I, Vale RD. T cell costimulatory receptor CD28 is a primary target for PD-1-mediated inhibition. Science. Mar. 31, 2017;355 (6332):1428-1433. doi: 10.1126/science. aaf1292. Epub Mar. 9, 2017. PMID: 28280247; PMCID: PMC6286077.

Cao J, Zou L, Luo P, Chen P, Zhang L. Increased production of circulating soluble co-stimulatory molecules CTLA-4, CD28 and CD80 in patients with rheumatoid arthritis. Int Immunopharmacol. Dec. 2012;14(4):585-92. doi: 10.1016/j.lntimp.2012.08.004. Epub Aug. 20, 2012. PMID: 22917707.

Chen YQ, Shi Hz. CD28/CTLA-4-CD80/CD86 and ICOS-B7RP-1 costimulatory pathway in bronchial asthma. Allergy. Jan. 2006;61(1):15-26. doi: 10.1111/j.1398-9995.2006.01008.x. PMID: 16364152.

Esensten JH, Helou YA, Chopra G, Weiss A, Bluestone JA. CD28 Costimulation: From Mechanism to Therapy. Immunity. May 17, 2016;44(5):973-88. doi: 10.1016/j.immuni.2016.04.020. PMID: 27192564; PMCID: PMC4932896.

Garcia-Chagollán M, Ledezma-Lozano IY, Hernández-Bello J, Sánchez-Hernández PE, Gutiérrez-Ureña SR, Muñoz-Valle JF. Expression patterns of CD28 and CTLA-4 in early, chronic, and untreated rheumatoid arthritis. J Clin Lab Anal. May 2020;34(5):e23188. doi: 10.1002/jcla.23188. Epub Jan. 6, 2020. PMID: 31907973; PMCID: PMC7246387.

PCT International Search Report for International Application No. PCT/IL2020/051243, mailed Mar. 24, 2021, 4pp.

PCT Written Opinion for International Application No. PCT/IL2020/051243, mailed Mar. 24, 2021, 7pp.

PCT International Preliminary Report on Patentability for International Application No. PCT/IL2020/051243, issued May 17, 2022, 8pp.

PCT International Search Report for International Application No. PCT/IL2020/050297, mailed Jun. 26, 2020, 5pp.

PCT Written Opinion for International Application No. PCT/IL2020/050297, mailed Jun. 26, 2020, 6pp.

* cited by examiner

| | Sequence | Theoretical MW | Experimental MW | |
|---|---|---|---|---|
| A | DABCYL – KGKHLSPSP | 1201.378 | 1201.504 | (SEQ ID NO: 12) |
| B | LFPGPSKPE + EDANS | 1219.403 | 1218.46 | (SEQ ID NO: 13) |
| C | DABCYL – KGKHLSPSP + Na | 1223.378 | 1223.49 | (SEQ ID NO: 12) |
| D | LFPGPSKPE + EDANS + Na | 1241.403 | 1240.448 | (SEQ ID NO: 13) |

Peptide – DABCYL-KGKHLSPSPLFPGPSKPE-EDANS ~ 2401.78 Da  (SEQ ID NO: 16)

136            144 | 145            152
KGKHLCPSP|LFPGPSKP  (SEQ ID NO: 9)

(SEQ ID NO: 9)

Figure 3D continued_1

METHODS OF IDENTIFYING AGENTS THAT BLOCK MCD28 CLEAVAGE BY MMPS

CROSS REFERENCE TO RELATED APPLICATIONS

This application is a National Phase of PCT Patent Application No. PCT/IL2020/051243 having International filing date of Dec. 2, 2020, which claims the benefit of priority of U.S. Provisional Patent Application No. 62/942, 240, filed Dec. 2, 2019, U.S. Provisional Patent Application No. 62/954,802, filed Dec. 30, 2019, and International Patent Application No. PCT/IL2020/050297, filed Mar. 12, 2020, the contents of which are all incorporated herein by reference in their entirety.

FIELD OF INVENTION

The present invention is in the field of immune regulation and immunotherapy.

BACKGROUND OF THE INVENTION

It is known that some co-stimulatory molecules have several physiological forms. Alongside membrane-bound forms, soluble forms have been described that are expressed in naive immune cells, increasing the complexity of T cell biology. The soluble form of CD28 (sCD28) has been ascribed to an alternatively spliced gene product and to active shedding of the membrane form of CD28 (mCD28). The splicing event results in a frame shift with the consequence of addition of two glutamate residues after glycine at position 137 before translational termination. The final product lacks the entire transmembrane and cytoplasmic regions and importantly is lacking the cysteine residue, at position 141, that mediates the disulfide linkage of dimeric CD28 (Magistrelli G., Biochem Biophy Res Commun, 1999). In contrast, much less is known about the mechanism of CD28 shedding and the exact site of cleavage, and the sequence of the shed sCD28 molecule are not known.

sCD28 has been shown to inhibit the immune response against cancer and has been correlated to autoimmune severity. Further, sCD28 inhibits the effect of PD-1 and PD-L1 based immunotherapies. As such, methods of inhibiting sCD28 production are greatly needed. In particular, methods and compositions that block the shedding of sCD28 are greatly needed. Blocking of sCD28 shedding has a double effect, in that it decreases sCD28 and increases mCD28 on immune cells. Both of these effects enhance immune surveillance against cancer.

SUMMARY OF THE INVENTION

The present invention provides methods of decreasing shedding of CD28, decreasing soluble CD28 levels, treating cancer and improving immunotherapies comprising inhibiting matrix metalloprotease-2 (MMP-2) and/or matrix metalloprotease-13 (MMP-13). Methods of producing agents for performance of the methods of the invention are also provided.

According to a first aspect, there is provided a method of decreasing shedding of CD28 from a surface of a cell expressing membranal CD28 (mCD28), the method comprising contacting the cell with a matrix metalloprotease-2 (MMP-2) inhibitor, a matrix metalloprotease-13 (MMP-13) inhibitor or both, thereby decreasing shedding of CD28 from a surface of a cell.

According to another aspect, there is provided a method of decreasing soluble CD28 (sCD28) levels in a subject in need thereof, the method comprising administering to the subject an MMP-2 inhibitor, an MMP-13 inhibitor or both, thereby decreasing sCD28 levels in a subject.

According to another aspect, there is provided a method of treating and/or preventing cancer in a subject in need thereof, the method comprising administering to the subject an MMP-2 inhibitor, an MMP-13 inhibitor or both, thereby treating and/or preventing cancer in the subject.

According to another aspect, there is provided a method of improving PD-1 and/or PD-L1 based immunotherapy in a subject in need thereof, the method comprising administering to the subject an MMP-2 inhibitor, an MMP-13 inhibitor or both, thereby improving PD-1 and/or PD-L1 based immunotherapy in a subject.

According to some embodiments, the subject in need of immunotherapy suffers from cancer.

According to some embodiments, the subject does not respond or lowly responds to PD-1 and/or PD-L1 based immunotherapy.

According to some embodiments, the subject's blood prior to the decreasing comprises at least 5 ng/mL sCD28.

According to some embodiments, the cancer is selected from melanoma, urothelial carcinoma, head and neck, non-small cell lung cancer, ovarian, kidney, gastric and colorectal.

According to some embodiments, the method increases mCD28 expression on a surface of the cell or in the subject, and/or increases mCD28-mediated immune cell activation in the cell or subject.

According to some embodiments, the method comprises administering an MMP-2 inhibitor.

According to some embodiments, the inhibitor is specific to MMP-2.

According to some embodiments, the inhibitor is specific to MMP-2 induced shedding of CD28.

According to some embodiments, the method comprises administering an MMP-13 inhibitor.

According to some embodiments, the inhibitor is specific to MMP-13.

According to some embodiments, the inhibitor is specific to MMP-13 induced shedding of CD28.

According to some embodiments, the inhibitor inhibits induced cleavage of mCD28 between P144 and L145 of mCD28.

According to some embodiments, the inhibitor binds mCD28 and inhibits MMP-2 induced shedding of CD28.

According to some embodiments, the inhibitor binds mCD28 and inhibits MMP-13 induced shedding of CD28.

According to some embodiments, the inhibitor binds a stalk region of mCD28, wherein the stalk region, a. comprises the amino acid sequence GKHLCPSPLFPGPSKP (SEQ ID NO: 7), KGKHLCPSPLFPGPS (SEQ ID NO: 8) or KGKHLCPSPLFPGPSKP (SEQ ID NO: 9);

b. consists of the amino acid sequence HVKGKHLCPSPLFPGPSKP (SEQ ID NO: 10); or c. both (a) and (b).

According to some embodiments, the inhibitor binds, occludes or blocks an MMP-2, MMP-13 or both cleavage site PX1X2/X3 wherein X3 is a hydrophobic residue, in the stalk region.

According to some embodiments, the cleavage site is PSPL and the MMP-2/MMP-13 cleaves between the P and the L.

According to some embodiments, the method of the invention further comprises administering another immunotherapy to the subject.

According to some embodiments, the immunotherapy is selected from:

a. a checkpoint inhibitor;

b. a chimeric antigen receptor (CAR) based therapy; and c. a cancer vaccine.

According to some embodiments, the checkpoint inhibitor is a PD-1 and/or PD-L1 based immunotherapy.

According to another aspect, there is provided a method for producing an agent for the performance of a method of the invention, the method comprising:

obtaining an agent that binds to a CD28 extracellular domain or fragment thereof, testing an ability of the agent to block cleavage of mCD28 by MMP-2, MMP-13 or both, and selecting at least one agent that blocks cleavage of mCD28 by MMP-2, MMP-13 or both; or culturing a host cell comprising one or more vectors comprising a nucleic acid sequence encoding an agent, wherein the nucleic acid sequence is that of an agent that was selected by:

i. obtaining an agent that binds to a CD28 extracellular domain or fragment thereof;

ii. testing an ability of the agent to block cleavage of mCD28 by MMP-2, MMP-13 or both; and iii. selecting at least one agent that blocks cleavage of mCD28 by MMP-2, MMP-13 or both;

thereby producing an agent for performance of a method of the invention.

According to some embodiments, obtaining an agent that binds specifically to CD28 extracellular domain or a fragment thereof is obtaining an agent that binds specifically to a CD28 stalk domain.

According to some embodiments, the agent that binds specifically to a CD28 stalk domain, binds specifically to an MMP-2, MMP-13 or both cleavage site in the CD28 stalk domain.

According to some embodiments, the cleavage site in the CD28 stalk domain is PSPL.

According to some embodiments, the method of the invention further comprises assaying mCD28 downstream signaling in the presence of the obtained agent and selecting at least one agent that neither substantially agonizes nor substantially antagonizes mCD28 signaling.

According to some embodiments, the method of the invention comprises testing an ability of said agent to block cleavage of mCD28 by MMP-2, and selecting at least one agent that blocks cleavage of mCD28 by MMP-2, or culturing a host cell comprising one or more vectors comprising a nucleic acid sequence encoding an agent, wherein the nucleic acid sequence is that of an agent that was selected by a method comprising testing an ability of said agent to block cleavage of mCD28 by MMP-2, and selecting at least one agent that blocks cleavage of mCD28 by MMP-2.

According to some embodiments, the method of the invention comprises testing an ability of said agent to block cleavage of mCD28 by MMP-13, and selecting at least one agent that blocks cleavage of mCD28 by MMP-13, or culturing a host cell comprising one or more vectors comprising a nucleic acid sequence encoding an agent, wherein the nucleic acid sequence is that of an agent that was selected by a method comprising testing an ability of said agent to block cleavage of mCD28 by MMP-13, and selecting at least one agent that blocks cleavage of mCD28 by MMP-13.

According to another aspect, there is provided an agent produced by a method of the invention.

According to another aspect, there is provided a pharmaceutical composition comprising an agent of the invention, and a pharmaceutically acceptable carrier, excipient or adjuvant.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
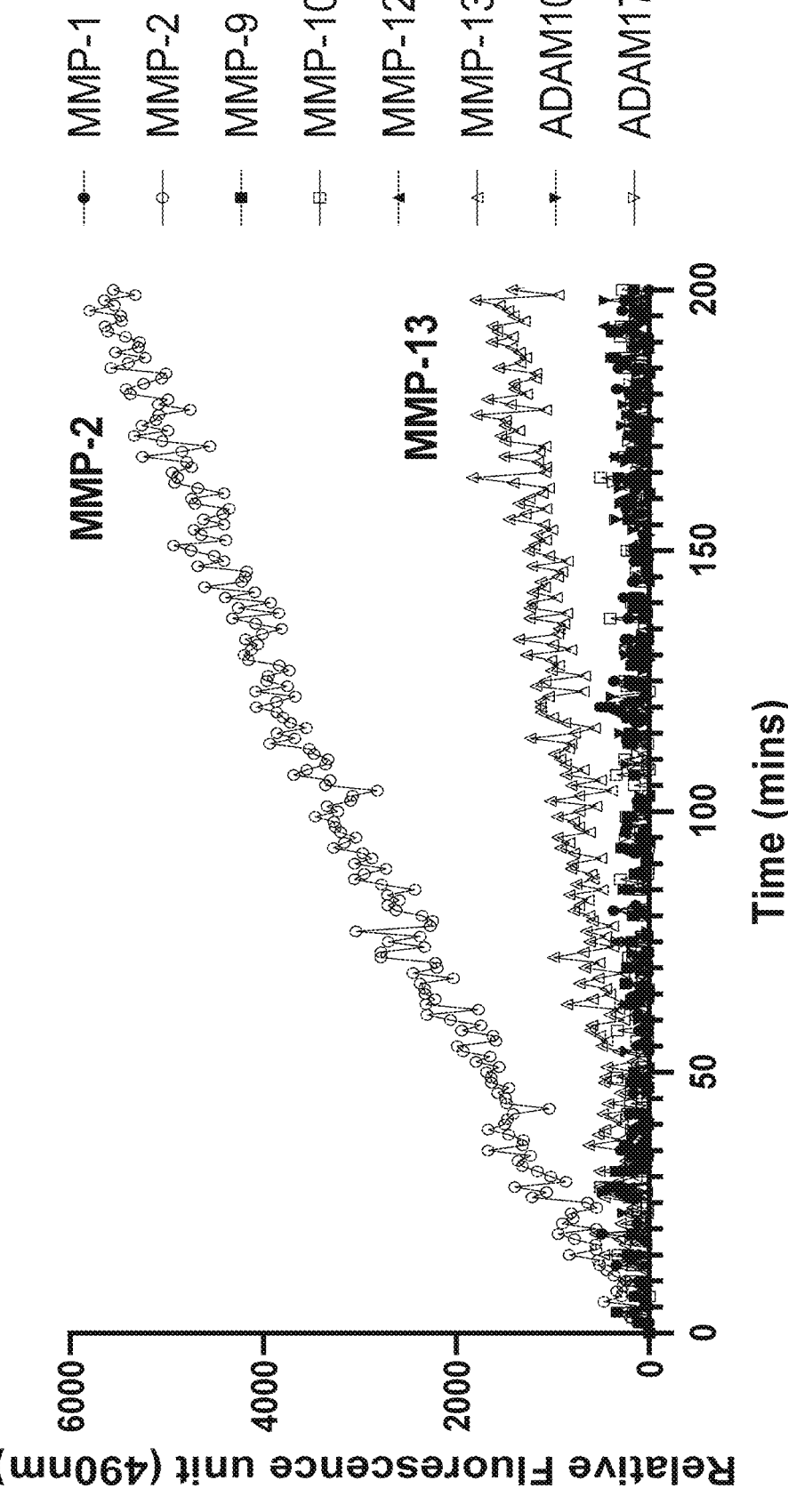
FIGS. 1A-1E. (1A-1E) Line graphs of fluorescence from quenched fluorogenic peptides of the human CD28 stalk region incubated with (1A) various recombinant human sheddases, (1B) varying concentrations of rhMMP-2, (1C) MMP-2 and various concentrations of the MMP-2 specific inhibitor ARP-100, (1D) varying concentrations of rhMMP-13, or (1E) MMP-13 and broad MMP inhibitor TMI-1.

The present invention, in some embodiments, provides methods of decreasing shedding of CD28, decreasing soluble CD28 levels, treating cancer and improving immunotherapies comprising inhibiting matrix metalloprotease-2 (MMP-2), matrix metalloprotease-13 (MMP-13) or both. The present invention further provides methods of producing agents for performance of the methods of the invention. The methods of the invention are based on the surprising finding that MMP-2 is the protease that is responsible and essential for the cleavage of membranal CD28 (mCD28) that produces soluble CD28 (sCD28). The method of the invention is further based on the surprising finding that MMP-13 also is responsible for the cleavage. Further, the exact cleavage site of MMP-2 and MMP-13 in the stalk region of CD28 has been discovered which allows for the production of agents that specifically block MMP-2/MMP-13 cleavage and shedding of CD28.

Anti-cleavage molecules have a double benefit. By blocking proteolytic cleavage of mCD28 they keep the amount of CD28 high on the cell surface of T cells. This allows for rapid and effective T cell activation, that would be impaired if the levels of surface CD28 dropped due to cleavage. Further, the reduction in cleavage leads to a reduction in sCD28 in a subject's blood stream, and thus a reduction in the deleterious effects of sCD28 on a subject's ability to fight cancer and the effectiveness of immunotherapy.

By a first aspect, there is provided a method of decreasing shedding of CD28 from a cell, the method comprising contacting the cell with a matrix metalloprotease-2 (MMP-2) inhibitor, a matrix metalloprotease-13 (MMP-13) inhibitor, or both thereby decreasing shedding of CD28 from a cell.

By another aspect, there is provided use of a matrix metalloprotease-2 (MMP-2) inhibitor, a matrix metalloprotease-13 (MMP-13) inhibitor or both for decreasing shedding of CD28 from a cell.

By another aspect, there is provided a method of decreasing soluble CD28 (sCD28) level in a subject in need thereof, the method comprising administering to the subject an MMP-2 inhibitor, an MMP-13 inhibitor or both, thereby decreasing sCD28 levels in a subject.

By another aspect, there is provided use of an MMP-2 inhibitor, an MMP-13 inhibitor or both, for decreasing soluble CD28 (sCD28) levels in a subject in need thereof.

By another aspect, there is provided a method of treating and/or preventing cancer in a subject in need thereof, the method comprising administering to the subject an MMP-2 inhibitor, an MMP-13 inhibitor or both, thereby treating and/or preventing cancer in the subject.

By another aspect, there is provided use of an MMP-2 inhibitor, an MMP-13 inhibitor or both, for treating and/or preventing cancer in a subject in need thereof.

By another aspect, there is provided a method of improving PD-1 and/or PD-L1 based immunotherapy in a subject in need thereof, the method comprising administering to said subject an MMP-2 inhibitor, an MMP-13 inhibitor or both, thereby improving PD-1 and/or PD-L1 based immunotherapy.

By another aspect, there is provided use of an MMP-2 inhibitor, an MMP-13 inhibitor or both, for improving PD-1 and/or PD-L1 based immunotherapy in a subject in need thereof.

In some embodiments, an MMP-2 inhibitor, an MMP-13 inhibitor or both, is an MMP-2 inhibitor. In some embodiments, an MMP-2 inhibitor, an MMP-13 inhibitor or both, is an MMP-13 inhibitor. In some embodiments, an MMP-2 inhibitor, an WIMP-13 inhibitor or both, is both an WIMP-2 inhibitor and an MMP-13 inhibitor. In some embodiments, both is two inhibitors one that inhibits WIMP-2 and one that inhibits MMP-13. In some embodiments, both is a single inhibitor that inhibits both WIMP-2 and WIMP-13.

In some embodiments, the CD28 is mammalian CD28. In some embodiments the CD28 is human CD28. In some embodiments, the human CD28 comprises or consists of the amino acid sequence:

(SEQ ID NO: 1)
MLRLLLALNLFPSIQVTGNKILVKQSPMLVAYDNAVNLSCKYSYNLF

SREFRASLHKGLDSAVEVCVVYGNYSQQLQVYSKTGFNCDGKLGNES

VTFYLQNLYVNQTDIYFCKIEVMYPPPYLDNEKSNGTIIHVKGKHLC

PSPLFPGPSKPFWVLVVVGGVLACYSLLVTVAFIIFWVRSKRSRLLH

SDYMNMTPRRPGPTRKHYQPYAPPRDFAAYRS.

In some embodiments, mature CD28 lacks a signal peptide and comprises or consists of the sequence:

(SEQ ID NO: 2)
NKILVKQSPMLVAYDNAVNLSCKYSYNLFSREFRASLHKGLDSAVEV

CVVYGNYSQQLQVYSKTGFNCDGKLGNESVTFYLQNLYVNQTDIYFC

KIEVMYPPPYLDNEKSNGTIIHVKGKHLCPSPLFPGPSKPFWVLVVV

8

-continued

GGVLACYSLLVTVAFIIFWVRSKRSRLLHSDYMNMTPRRPGPTRKHY

QPYAPPRDFAAYRS.

In some embodiments, the DNA coding sequence that codes for full length human CD28 comprises the sequence:

(SEQ ID NO: 3)
ATGCTCAGGCTGCTCTTGGCTCTCAACTTATTCCCTTCAATTCAAGT

AACAGGAAACAAGATTTTGGTGAAGCAGTCGCCCATGCTTGTAGCGT

ACGACAATGCGGTCAACCTTAGCTGCAAGTATTCCTACAATCTCTTC

TCAAGGGAGTTCCGGGCATCCCTTCACAAAGGACTGGATAGTGCTGT

GGAAGTCTGTGTTGTATATGGGAATTACTCCCAGCAGCTTCAGGTTT

ACTCAAAAACGGGGTTCAACTGTGATGGGAAATTGGGCAATGAATCA

GTGACATTCTACCTCCAGAATTTGTATGTTAACCAAACAGATATTTA

CTTCTGCAAAATTGAAGTTATGTATCCTCCTCCTTACCTAGACAATG

AGAAGAGCAATGGAACCATTATCCATGTGAAAGGGAAACACCTTTGT

CCAAGTCCCCTATTTCCCGGACCTTCTAAGCCCTTTTGGGTGCTGGT

GGTGGTTGGTGGAGTCCTGGCTTGCTATAGCTTGCTAGTAACAGTGG

CCTTTATTATTTTCTGGGTGAGGAGTAAGAGGAGCAGGCTCCTGCAC

AGTGACTACATGAACATGACTCCCCGCCGCCCCGGGCCCACCCGCAA

GCATTACCAGCCCTATGCCCCACCACGCGACTTCGCAGCCTATCGCT

CCTGA.

In some embodiments, CD28 is sCD28. In some embodiments, CD28 is mCD28. As used herein, sCD28 refers to any CD28 fragment or variant that does not comprise a transmembrane domain and thus cannot be integrated in a membrane. In some embodiments, the CD28 transmembrane domain comprises the amino acid sequence FWVLVVVGGVLACYSLLVTVAFIIFWV (SEQ ID NO: 4). In some embodiments, sCD28 is not membrane bound. In some embodiments, sCD28 is in solution. In some embodiments, the sCD28 is CD28 in blood. In some embodiments, the sCD28 is CD28 in the TME. In some embodiments, sCD28 is CD28 in a bodily fluid. In some embodiments, sCD28 is a cleavage product from membranal CD28 (mCD28). In some embodiments, sCD28 is truncated CD28. In some embodiments, sCD28 lacks the cytoplasmic domain of full-length CD28. In some embodiments, sCD28 is dimeric sCD28. In some embodiments, sCD28 is monomeric sCD28. In some embodiments, sCD28 is not a splice variant arising from alternative splicing of CD28. In some embodiments, sCD28 comprises the amino acid sequence: MLRLLLALNLFPSIQVTGNKILVKQSPMLVAYD-NAVNLSCKYSYNLFSREFRASLHKG LDSAVEVCV-VYGNYSQQLQVYSKTGFNCDGKLGNESVTFYLQN-LYVNQTDIYFCKIE VMYPPPYLDNEKSNGTIIHVKGKHLCPSP (SEQ ID NO: 5). In some embodiments, sCD28 lacks the signal peptide and comprises the sequence: NKIL-VKQSPMLVAYDNAVNLSCKYSYNLFSRE-FRASLHKGLDSAVEVCVVYGNYSQQ LQVYSKTGFNCDGKLGNESVTFYLQNLY-VNQTDIYFCKIEVMYPPPYLDNEKSNGTIIH VKGKHLCPSP (SEQ ID NO: 6). In some embodiments, sCD28 consists of SEQ ID NO: 5. In some embodiments, sCD28 consists of SEQ ID NO: 6.

In some embodiments, the inhibitor inhibits MMP-2 protease activity. In some embodiments, the inhibitor inhibits MMP-2 sheddase activity. In some embodiments, the inhibitor inhibits MMP-2 binding to CD28. In some embodiments, the inhibitor inhibits MMP-2 binding to mCD28. In some embodiments, the inhibitor is specific to MMP-2. As used herein, the term "specific" refers to the inhibitor substantially inhibiting/binding MMP-2, MMP-13 or both and not substantially inhibiting/binding other proteases. In some embodiments, the inhibitor does not inhibit any proteases other than MMP-2. In some embodiments, the inhibitor directly inhibits MMP-2. In some embodiments, the inhibitor binds MMP-2. In some embodiments, the inhibitor specifically binds MMP-2. In some embodiments, the inhibitor does not bind any proteases other than MMP-2. In some embodiments, the inhibitor binds other proteases other than MMP-2 but does not substantially inhibit those other proteases. In some embodiments, non-inhibition is inhibition at or below 50, 45, 40, 35, 30, 25, 20, 15, 10, 9, 8, 7, 6, 5, 4, 3, 2, or 1%. Each possibility represents a separate embodiment of the invention. In some embodiments, the inhibitor is specific to MMP-2 and at least one of ADAM 10 and ADAM 17. In some embodiments, the inhibitor is specific to MMP-2 and at least one of MMP-13, ADAM 10 and ADAM 17. In some embodiments, the inhibitor is specific to MMP-2 and MMP-13. In some embodiments, the inhibitor is specific to MMP-2 cleavage of mCD28. In some embodiments, the inhibitor is specific to MMP-2 induced cleavage of mCD28. In some embodiments, the inhibitor is specific to MMP-2 mediated cleavage of mCD28. In some embodiments, MMP-2 cleavage of mCD28 is between P144 and L145 of CD28. In some embodiments, P144 and L145 are of SEQ ID NO: 1. In some embodiments, MMP-2 cleavage of mCD28 is between P144 and L145 of SEQ ID NO: 1. In some embodiments, MMP-2 cleavage of mCD28 is between P129 and L130 of SEQ ID NO: 2.

In some embodiments, the inhibitor inhibits MMP-13 protease activity. In some embodiments, the inhibitor inhibits MMP-13 sheddase activity. In some embodiments, the inhibitor inhibits MMP-13 binding to CD28. In some embodiments, the inhibitor inhibits MMP-13 binding to mCD28. In some embodiments, the inhibitor is specific to MMP-13. In some embodiments, the inhibitor does not inhibit any proteases other than MMP-13. In some embodiments, the inhibitor directly inhibits MMP-13. In some embodiments, the inhibitor binds MMP-13. In some embodiments, the inhibitor specifically binds MMP-13. In some embodiments, the inhibitor does not bind any proteases other than MMP-13. In some embodiments, the inhibitor binds other proteases other than MMP-13 but does not substantially inhibit those other proteases. In some embodiments, the inhibitor is specific to MMP-13 and at least one of ADAM 10 and ADAM 17. In some embodiments, the inhibitor is specific to MMP-13 and at least one of MMP-2, ADAM 10 and ADAM 17. In some embodiments, the inhibitor is specific to MMP-13 and MMP-9. In some embodiments, inhibitor does not significantly inhibit ADAM10 or ADAM17. In some embodiments, the inhibitor is specific to MMP-13, MMP-2 and MMP-9. In some embodiments, the inhibitor is specific to MMP-13, MMP-2 and MMP-3. In some embodiments, the inhibitor is specific to MMP-13 cleavage of mCD28. In some embodiments, the inhibitor is specific to MMP-13 induced cleavage of mCD28. In some embodiments, the inhibitor is specific to MMP-13 mediated cleavage of mCD28. In some embodiments, MMP-13 cleavage of mCD28 is between P144 and L145 of CD28. In some embodiments, P144 and L145 are of SEQ ID NO: 1. In some embodiments, MMP-13 cleavage of mCD28 is between P144 and L145 of SEQ ID NO: 1. In some embodiments, MMP-13 cleavage of mCD28 is between P129 and L130 of SEQ ID NO: 2.

In some embodiments, only an MMP-2 inhibitor is administered. In some embodiments, only an MMP-13 inhibitor is administered. In some embodiments, an MMP-2 inhibitor and not an MMP-13 inhibitor is administered. In some embodiments, an MMP-13 inhibitor and not an MMP-2 inhibitor is administered. In some embodiments, neither an ADAM10 nor an ADAM17 inhibitor is administered. In some embodiments, an ADAM10 inhibitor is not administered. In some embodiments, an ADAM17 inhibitor is not administered. In some embodiments, only an MMP-2 inhibitor is contacted. In some embodiments, only an MMP-13 inhibitor is contacted. In some embodiments, an MMP-2 inhibitor and not an MMP-13 inhibitor is contacted. In some embodiments, an MMP-13 inhibitor and not an MMP-2 inhibitor is contacted. In some embodiments, neither an ADAM10 nor an ADAM17 inhibitor is contacted. In some embodiments, an ADAM10 inhibitor is not contacted. In some embodiments, an ADAM17 inhibitor is not contacted.

In some embodiments, inhibition is at least a 10, 20, 25, 30, 40, 50, 60, 70, 75, 80, 85, 90, 95, 97, 99 or 100% inhibition. Each possibility represents a separate embodiment of the invention. In some embodiments, inhibition is complete inhibition. In some embodiments, inhibition is blocking. In some embodiments, the inhibition is partial inhibition.

In some embodiments, the inhibitor is a small molecule inhibitor. In some embodiments, the inhibitor is a small molecule inhibitor of MMP-2. Examples of MMP-2 inhibitors include, but are not limited to: ARP-100, Batimastat, Marimastat, Tanomastat, rebimastat, prinomastat, and Neovastat. In some embodiments, the inhibitor is a monoclonal antibody inhibitor of MMP-2. Examples of antibody-based MMP-2 inhibitors include, but are not limited to, DX-2400, SDS3 and SDS4. In some embodiments, the small molecule inhibitor of MMP-2 is ARP-100.

In some embodiments, the inhibitor is a small molecule inhibitor of MMP-13. Examples of MMP-13 inhibitors include, but are not limited to: CL82198 hydrochloride, 4-N,6-N-bis[(4-fluoro-3-methylphenyl)methyl]pyrimidine-4,6-dicarboxamide, and WAY170523. In some embodiments, the inhibitor is a monoclonal antibody inhibitor of MMP-13. Examples of antibody-based MMP-13 inhibitors include, but are not limited to, C-3 and MM0019-12E10.

In some embodiments, the inhibitor is a small molecule inhibitor of MMP-2 and MMP-13. Examples of inhibitors of both proteins include, but are not limited to: PD166793. In some embodiments, the inhibitor is a small molecule inhibitor of MMP-9 and MMP-13. Examples of inhibitors of both proteins include, but are not limited to: N-Hydroxy-1-(4-methoxyphenyl)sulfonyl-4-(4-biphenylcarbonyl)piperazine-2-carboxamide and 3-[(Hydroxyamino)carbonyl]-4-[(4-methoxyphenyl)sulfonyl]-1-piperazinecarboxylic acid phenylmethyl ester (204139-85-5).

In some embodiments, the inhibitor is a small molecule pan MMP inhibitor. Examples of pan-MMP inhibitors include, but are not limited to actinonin, MMP inhibitor V, N'-hydroxy-N-[1-(methylcarbamoyl)-3-phenyl-propyl]-2-(2-methylpropyl)butanediamide and CP471474. In some embodiments, the inhibitor does not inhibit ADAM10. In some embodiments, the inhibitor does not inhibit ADAM17. In some embodiments, the inhibitor does not inhibit ADAM10 or ADAM17. In some embodiments, the inhibitor is not an ADAM inhibitor. Small molecule inhibitors and antibody inhibitors are well known in the art and may be purchased commercially, for examples from Santa Cruz Biotechnology.

In some embodiments, the inhibitor is an antibody or antigen binding fragment thereof. In some embodiments, the antibody or fragment is fused to another protein or fragment of a protein. In some embodiments, the second protein or fragment increases half-life. In some embodiments, half-life is serum half-life. In some embodiments, the half-life extending protein is human serum albumin. In some embodiments, the inhibitor is modified by a chemical that produces a modification that enhances half-life. In some embodiments, the modification is PEGylation and the chemical is polyethylene glycol. In some embodiments, the inhibitor is PEGylated. A skilled artisan will appreciate that any half-life extending protein or chemical agent, or modification known in the art may be used.

In some embodiments, the inhibitor binds as a monomer. In some embodiments, the inhibitor binds as a dimer. In some embodiments, the inhibitor binds as a monomer and/or a dimer. In some embodiments, the inhibitor binds as a dimer, but does not crosslink and/or activate mCD28. In some embodiments, the inhibitor binds as a dimer, but only binds a single molecule of CD28. In some embodiments, the inhibitor binds monomeric CD28. In some embodiments, the inhibitor binds dimeric CD28. In some embodiments, the inhibitor binds monomeric and/or dimeric CD28.

In some embodiments, the inhibitor is not a CD28 agonist. In some embodiments, the inhibitor is not a CD28 antagonist. In some embodiments, the inhibitor is neither a CD28 agonist nor antagonist.

In some embodiments, the inhibitor does not bind the ligand binding domain of mCD28. In some embodiments, the inhibitor does not obscure or block access to the ligand binding domain. In some embodiments, the inhibitor binds the cleavage site. In some embodiments, the inhibitor obscures, occludes or blocks access to the cleavage site. In some embodiments, the inhibitor binds, blocks, occludes or obscures the MMP-2 cleavage site. In some embodiments, the inhibitor does not bind the MMP-2 cleavage site but occludes the site. In some the inhibitor blocks access to the MMP-2 cleavage site. In some embodiments, the inhibitor generates steric hinderance than blocks the MMP-2 cleavage site. In some embodiments, the inhibitor does not bind the MMP-2 cleavage site but binding of the inhibitor generates a conformational change to mCD28 that blocks the MMP-2 cleavage site. In some embodiments, binding of the inhibitor generates a conformational change to CD28 that blocks the MMP-2 cleavage site. In some embodiments, the inhibitor binds the stalk domain. In some embodiments, the inhibitor binds the CD28 extracellular domain. In some embodiments, the inhibitor binds the CD28 extracellular domain but not the stalk domain. In some embodiments, the MMP-2 cleavage motif is PX1X2/X3 (SEQ ID NO: 14), wherein the last X3 is a hydrophobic residue. In some embodiments, the PX1X2/X3 motif in CD28 is PSP/L. In some embodiments, the PX1X2/X3 motif is PSP/L (SEQ ID NO: 15). In some embodiments, the protease cleavage site is amino acids 142-145 (PSPL) of SEQ ID NO: 1. In some embodiments, the protease cleavage site is amino acids 127-130 (PSPL) of SEQ ID NO: 2. In some embodiments, the protease cleavage site is amino acids 9-12 (PSPL) of SEQ ID NO: 10. In some embodiments, the protease is MMP-2. In some embodiments, the protease is MMP-13. In some embodiments, the protease is MMP-2 or MMP-13. In some embodiments, the protease is MMP-2 and MMP-13. In some embodiments, the inhibitor blocks accesses of the protease to the cleavage site. In some embodiments, the inhibitor binds a stalk region of CD28. In some embodiments, the inhibitor binds, blocks, occludes or obscures the MMP-13 cleavage site. In some the inhibitor blocks access to the MMP-13 cleavage site. In some embodiments, the inhibitor does not bind the MMP-13 cleavage site but occludes the site. In some the inhibitor blocks access to the MMP-13 cleavage site. In some embodiments, the inhibitor generates steric hinderance than blocks the MMP-13 cleavage site. In some embodiments, the inhibitor does not bind the MMP-13 cleavage site but binding of the inhibitor generates a conformational change to mCD28 that blocks the MMP-13 cleavage site. In some embodiments, binding of the inhibitor generates a conformational change to CD28 that blocks the MMP-13 cleavage site. In some embodiments, the MMP-13 cleavage motif is PX1X2/X3 (SEQ ID NO: 14), wherein the last X3 is a hydrophobic residue.

In some embodiments, the inhibitor binds mCD28. In some embodiments, the inhibitor binds a stalk region of mCD28. In some embodiments, the inhibitor binds a membrane proximal region of mCD28. In some embodiments, the stalk region comprises the sequence GKHLCPSPLFPGPSKP (SEQ ID NO: 7). In some embodiments, the stalk region comprises the sequence KGKHLCPSPLFPGPS (SEQ ID NO: 8). In some embodiments, the stalk region comprises the sequence KGKHLCPSPLFPGPSKP (SEQ ID NO: 9). In some embodiments, the stalk region comprises the sequence HVKGKHLCPSPLFPGPSKP (SEQ ID NO: 10). In some embodiments, the stalk region consists of SEQ ID NO: 7. In some embodiments, the stalk region consists of SEQ ID NO: 8. In some embodiments, the stalk region consists of SEQ ID NO: 9. In some embodiments, the stalk region consists of SEQ ID NO: 10. In some embodiments, the inhibitor binds monomeric sCD28. In some embodiments, the inhibitor binds dimeric sCD28. In some embodiments, the inhibitor binds monomeric sCD28, dimeric sCD28 or both. In some embodiments, the inhibitor binds monomeric but not dimeric sCD28. In some embodiments, the inhibitor binds dimeric but not monomeric sCD28. In some embodiments, the inhibitor does not bind sCD28.

An example of an inhibitor that binds mCD28 includes, but is not limited to, an antibody, an antigen binding fragment of an antibody, a nanobody, a single chain antibody, a single domain antibody, a small molecule, a peptide and a DARPin. In some embodiments, the inhibitor is selected from an antibody, an antigen binding fragment of an antibody, a Fab fragment, a nanobody, a single chain antibody, a single domain antibody, a small molecule, a peptide and a DARPin. In some embodiments, the inhibitor is selected from an antibody, an antigen binding fragment of an antibody, a Fab fragment, a single chain antibody, a single domain antibody, a small molecule, and a peptide with specific binding to CD28. In some embodiments, the inhibitor is a single domain antibody. In some embodiments, the inhibitor is a nanobody. In some embodiments, the agent is a VHH antibody. In some embodiments, the agent is a VNAR. In some embodiments, the agent is a camelid antibody. In some embodiments, the antibody is a shark antibody. As used herein, the terms "single domain antibody" and "nanobody" are synonymous and used interchangeably. In some embodiments, the peptide has specific binding to CD28. In some embodiments, the inhibitor is a peptide with specific binding to CD28. In some embodiments, the peptide is selected from an antibody, an antigen binding fragment of an antibody, a Fab fragment, a single chain antibody, a single-domain antibody, a nanobody, a VHH antibody, a VNAR and an antibody mimetic. As used herein, the term "antibody mimetic" refers to an organic compound that can specifically bind to a target antigen. In some embodiments, an antibody mimetic is not structurally related to an antibody. Examples of antibody mimetics include, but are not limited to, affilins, affimers, affitins, alphabodies, anticalins, avimers, DARPins, fynomers, Kunitz domain peptides, monobodies, and nanoCLAMPS. In some embodiments, the antibody mimetic is a DARPin. All of these agents are well known in the art and are known to be useful in blocking protein-protein interactions, e.g. interactions between receptors and their ligands. Small molecules and proteins that can bind mCD28 may occlude the cleavage site or may cause hinderance or impair access for the protease. In some embodiments, the protein is an antibody mimetic. As used herein, the term "DARPin" refers to a designed ankyrin repeat protein. DARPins are genetically engineered antibody mimetic proteins that are generally highly specific for their protein target. Thus, a DARPin for CD28 may be an example of an agent.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody comprises IgG2 or IgG4. In some embodiments, the antibody comprises IgG2. In some embodiments, the antibody comprises IgG4.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt.cines.fr/) (IMGT®/V-Quest) to identify variable region segments, including CDRs. See, e.g., Brochet, X. et al, Nucl. Acids Res. J6:W503-508 (2008).

Chothia et al. also defined a numbering system for variable domain sequences that is applicable to any antibody. One of ordinary skill in the art can unambiguously assign this system of "Chothia numbering" to any variable domain sequence, without reliance on any experimental data beyond the sequence itself. As used herein, "Chothia numbering" refers to the numbering system set forth by Chothia et al., Journal of Molecular Biology, "Canonical Structures for the Hypervariable regions of immunoglobulins" (1987) and Chothia et al., Nature, "Conformations of Immunoglobulin Hypervariable Regions" (1989).

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies and is not to be construed as produced by any specific preparation method. Monoclonal antibodies to be used in accordance with the methods provided herein, may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies production is known in the art and is described in Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include: antibodies, fragments of antibodies, Fab and F(ab')2, single-domain antigen-binding recombinant fragments and natural nanobodies. In some embodiments, the antigen binding fragment is selected from the group consisting of a Fv, Fab, F(ab')$_2$, scFV or a scFV$_2$ fragment.

In some embodiments, the present invention provides nucleic acid sequences encoding the antibodies or antigen binding portions of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

In some embodiments, decreasing sCD28 levels is by at least 5, 10, 15, 20, 25, 30, 35, 40, 45, 50, 55, 60, 65, 70, 75, 80, 85, 90, 95, 97 or 99%. Each possibility represents a separate embodiment of the invention. In some embodiments, reduction in sCD28 levels is to that of a healthy individual. In some embodiments, the reduction reduces sCD28 levels to at most 1, 2, 3, 4, 5, 10, 15, 20, 25, 30, 35, 40, 45, or 50 ng/mL. Each possibility represents a separate embodiment of the invention. In some embodiments, the reduction reduces sCD28 blood levels to at most 5 ng/mL. In some embodiments, the reduction reduces sCD28 blood levels to at most 10 ng/mL. In some embodiments, the reduction reduces sCD28 blood levels to at most 20 ng/mL. In some embodiments, the reduction reduces sCD28 levels to that of a healthy individual. In some embodiments, the reduction reduces sCD28 levels to below 1, 2, 3, 4, 5, 10, 15, 20, 25, 30, 35, 40, 45, or 50 ng/mL. Each possibility represents a separate embodiment of the invention. In some embodiments, the reduction reduces sCD28 levels to below 5 ng/mL. In some embodiments, the reduction reduces sCD28 levels to below 10 ng/mL. In some embodiments, the reduction reduces sCD28 levels to below 20 ng/mL.

In some embodiments, sCD28 levels are reduced in a subject. In some embodiments, in a subject is in the blood of a subject. In some embodiments, the reducing or decreasing occurs in blood, peripheral blood or the TME of the subject. In some embodiments, the reducing or decreasing occurs in blood. In some embodiments, the reducing or decreasing occurs in peripheral blood. In some embodiments, the reducing or decreasing occurs in the TME.

In some embodiments, sCD28 levels are as measured by ELISA. In some embodiments, the ELISA is a sandwich ELISA. In some embodiments, the ELISA is a standardized sandwich ELISA. In some embodiments, the ELISA is a Bender MedSystems ELISA. In some embodiments, the ELISA is Bender MedSystems ELISA kit BMS290. In some embodiments, the ELISA is performed with an agent of the invention.

As used herein, decreasing proteolytic cleavage, decreasing shedding, and decreasing cleavage all are used synonymously and refer to any reduction in proteolytic cleavage of mCD28. In some embodiments, decreasing is inhibiting. In some embodiments, the decreasing is a reduction in cleavage of at least 5, 10, 15, 20, 25, 30, 35, 40, 45, 50, 55, 60, 65, 70, 75, 80, 85, 90, 95, 97, 99 or 100%. Each possibility represents a separate embodiment of the invention. In some embodiments, inhibiting proteolytic cleavage maintains levels of mCD28 on immune cells. In some embodiments, inhibiting proteolytic cleavage maintains a level of mCD28 on immune cells. In some embodiments, inhibiting proteolytic cleavage increases levels of mCD28 on immune cells. In some embodiments, inhibiting proteolytic cleavage increases a level of mCD28 on immune cells. In some embodiments, inhibiting proteolytic cleavage maintains levels of mCD28 adequate for immune-stimulation. In some embodiments, the immune cells are in the subject.

In some embodiments, the decrease in shedding is from a surface of a cell. In some embodiments, the cell is a cell that expresses mCD28. In some embodiments, the cell is an immune cell. In some embodiments, the immune cell is a T cell. In some embodiments, the cell is a cancer cell.

In some embodiments, the inhibitor does not modulate CD28 function and/or signaling. In some embodiments, the inhibitor does not decrease CD28 function and/or signaling. In some embodiments, the inhibitor increases CD28 function and/or signaling. It will be understood by a skilled artisan that by increasing the amount of mCD28 on immune cells, CD28 signaling in the cells will be increased. In some embodiments, the increase in signaling is an indirect increase. In some embodiments, the inhibitor does not directly increase CD28 function and/or signaling. In some embodiments, inhibitor is not a CD28 agonist and inhibition of cleavage increases mCD28 levels on a cell surface which increases CD28 signaling in the cell. In some embodiments, the inhibitor does not degrade mCD28. In some embodiments, the inhibitor does not lead to or facilitate mCD28 degradation. In some embodiments, the signaling is mCD28-mediated immune cell activation. In some embodiments, the inhibitor does not inhibit immune cell activation. In some embodiments, the inhibitor does not induce CD28 receptor internalization or recycling. Co-stimulation via mCD28 is essential for immune activation of T-cells. Proteolytic cleavage removed the ligand-binding domain in the extracellular region of CD28 from the transmembrane and cytoplasmic portions of the protein which remain in the membrane. Thus, cleaved CD28 cannot signal and cannot contribute to T cell activation. Thus, an agent that blocks cleavage, and is also an antagonist does not allow for mCD28 activation. Similarly, an agent that blocks cleavage, but is also an agonist could induce aberrant T-cell activation, and potentially an autoimmune response. In some embodiments, the inhibitor is not anti-CD28 antibody MAB342. In some embodiments, the inhibitor is not anti-CD28 antibody clone #37407.

In some embodiments, the inhibitor does not reduce surface levels of mCD28 on an immune cell. In some embodiments, the immune cell is a T cell. In some embodiments, the inhibitor reduces surface levels of mCD28 by less than 50, 40, 30, 25, 20, 15, 10, 7, 5, 3, 2 or 1%. Each possibility represents a separate embodiment of the invention.

In some embodiments, the immunotherapy is PD-1 and/or PD-L1 based immunotherapy. In some embodiments, the immunotherapy is PD-1 based immunotherapy. In some embodiments, the immunotherapy is PD-L1 based immunotherapy. In some embodiments, the PD-1/PD-L1 based immunotherapy comprises administering an anti-PD1 or anti-PD-L1 antibody. In some embodiments, the therapy comprises blockade of the PD-1 checkpoint. In some embodiments, the immunotherapy is CD80 based immunotherapy. In some embodiments, the immunotherapy is CD86 based immunotherapy. In some embodiments, the immunotherapy comprises administering allogenic, syngenic or autologous immune cells to the subject. In some embodiments, the immune cells are T cells. In some embodiments, the subject in need of immunotherapy suffers from cancer.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

In some embodiments, the decreasing comprises administering to the subject at least one agent of the invention. As used herein, the terms "administering," "administration," and like terms refer to any method which, in sound medical practice, delivers a composition containing an active agent to a subject in such a manner as to provide a therapeutic effect. One aspect of the present subject matter provides for oral administration of a therapeutically effective amount of an agent of the invention to a patient in need thereof. Other suitable routes of administration can include parenteral, subcutaneous, intravenous, intramuscular, or intraperitoneal.

In some embodiments, decreasing comprises administering a peptide comprising the MMP-2 binding or cleavage motif of CD28. In some embodiments, the peptide is monomeric. In some embodiments, the peptide is dimeric. In some embodiments, the CD28 is human CD28. In some embodiments, the peptide inhibits access of the protease to the cleavage site. In some embodiments, the peptide induces production of autoantibodies that block the cleavage site. In some embodiments, the peptide comprises or consists of the sequence PSPL. In some embodiments, the peptide comprises the sequence PSPL.

In some embodiments, the subject's blood comprises elevated levels of sCD28. In some embodiments, the subject's blood before the decreasing comprises elevated levels of sCD28. In some embodiments, the levels are elevated above those of healthy subjects. In some embodiments, the subject's sCD28 levels are elevated by at least 5%, 10%, 15%, 20%, 25%, 30%, 40%, 50%, 60%, 70%, 80%, 90%, 100%, 150%, 200%, 250%, 300%, 350%, 400%, 500%, 600%, 700%, 800%, 900%, or 1000% above healthy subject levels. Each possibility represents a separate embodiment of the invention. In some embodiments, the levels are elevated above 5, 6, 7, 8, 9, 10, 12, 14, 15, 16, 18, 20, 25, 30, 35, 40, 45 or 50 ng/mL of blood. Each possibility represents a separate embodiment of the invention. In some embodiments, the levels are elevated above 5 ng/mL. In some embodiments, the levels are elevated above 10 ng/mL. In some embodiments, the levels are elevated above 20 ng/mL. In some embodiments, the subject's blood comprises at least 5, 6, 7, 8, 9, 10, 12, 14, 15, 16, 18, 20, 25, 30, 35, 40, 45 or 50 ng sCD28 per mL of blood. Each possibility represents a separate embodiment of the invention. In some embodiments, the subject's blood prior to the decreasing comprises at least 5, 6, 7, 8, 9, 10, 12, 14, 15, 16, 18, 20, 25, 30, 35, 40, 45 or 50 ng sCD28 per mL of blood. Each possibility represents a separate embodiment of the invention. In some embodiments, the subject's blood comprises at least 5 ng/mL sCD28. In some embodiments, the subject's blood comprises at least 10 ng/mL sCD28. In some embodiments, the subject's blood comprises at least 20 ng/mL sCD28. In some embodiments, the subject's blood prior to the decreasing comprises at least 5 ng/mL sCD28. In some embodiments, the subject's blood prior to the decreasing comprises at least 10 ng/mL sCD28. In some embodiments, the subject's blood prior to the decreasing comprises at least 20 ng/mL sCD28.

In some embodiments the subject's blood comprises healthy levels of sCD28. In some embodiments, the subject's blood does not comprise elevated levels. In some embodiments, the subject's blood comprises at most 0, 1, 2, 3, 4, or 5 ng sCD28 per mL of blood. Each possibility represents a separate embodiment of the invention. In some embodiments, the subjects blood comprises less than 5 ng/mL sCD28. In some embodiments, the subjects blood comprises less than 2 ng/mL sCD28. It will be understood that when a subject's blood does not have elevated sCD28 the administration of an MMP-2/MMP-13 inhibitor is a preventative or prophylactic measure. Such a preventative measure may be administered to a subject that is cancer free, a subject that suffers from cancer but does not have elevated sCD28 levels, a subject that is in cancer regression and a subject that is receiving other cancer therapy concomitantly.

In some embodiments, the subject suffers from cancer. In some embodiments, the cancer is a cancer that can be treated with PD-1/PD-L1 therapy. In some embodiments, the subject has undergone PD-1/PD-L1 therapy. In some embodiments, the subject is a non-responder to PD-1/PD-L1 therapy. In some embodiments, the subject is naïve to PD-1/PD-L1 therapy. In some embodiments, the methods of the invention are performed together with PD-1/PD-L1 therapy. In some embodiments, the methods of the invention are performed before PD-1/PD-L1 therapy.

In some embodiments, the method further comprises administering another immunotherapy to the subject. In some embodiments, the method further comprises administering a PD-1 and/or PD-L1 based immunotherapy. In some embodiments, the another immunotherapy is a checkpoint inhibitor. In some embodiments, the checkpoint inhibitor is a PD-1 and/or PD-L1 inhibitor. In some embodiments, the checkpoint inhibitor is a CTLA-4 inhibitor. In some embodiments, the another immunotherapy is a chimeric antigen receptor (CAR) based immunotherapy. In some embodiments, the CAR is a CAR-T. In some embodiments, the CAR is a CAR-NK. In some embodiments, the another immunotherapy is a cancer vaccine.

As used herein, the terms "CAR-T cell" and "CAR-NK cell" refer to an engineered receptor which has specificity for at least one protein of interest (for example an immunogenic protein with increased expression following treatment with an epigenetic modifying agent) and is grafted onto an immune effector cell (a T cell or NK cell). In some embodiments, the CAR-T cell has the specificity of a monoclonal antibody grafted onto a T-cell. In some embodiments, the CAR-NK cell has the specificity of a monoclonal antibody grafted onto a NK-cell. In some embodiments, the T cell is selected from a cytotoxic T lymphocyte and a regulatory T cell.

CAR-T and CAR-NK cells and their vectors are well known in the art. Such cells target and are cytotoxic to the protein for which the receptor binds. In some embodiments, a CAR-T or CAR-NK cell targets at least one viral protein. In some embodiments, a CAR-T or CAR-NK cell targets a plurality of viral proteins. In some embodiments, a CAR-T or CAR-NK cell targets a viral protein with increased expression due to contact with an epigenetic modifying agent.

Construction of CAR-T cells is well known in the art. In one non-limiting example, a monoclonal antibody to a viral protein can be made and then a vector coding for the antibody will be constructed. The vector will also comprise a costimulatory signal region. In some embodiments, the costimulatory signal region comprises the intracellular domain of a known T cell or NK cell stimulatory molecule. In some embodiments, the intracellular domain is selected from at least one of the following: CD3Z, CD27, CD28, 4-1BB, OX40, CD30, CD40, PD-1, ICOS, lymphocyte function-associated antigen-1 (LFA-1), CD2, CD 7, LIGHT, NKG2C, B7-H3, and a ligand that specifically binds with CD83. In some embodiments, the vector also comprises a CD3Z signaling domain. This vector is then transfected, for example by lentiviral infection, into a T-cell.

In some embodiments, the cancer is a cancer with elevated sCD28 levels. In some embodiments, the cancer is a cancer characterized by elevated sCD28 levels. In some embodiments, the cancer comprises high sCD28 levels. In some embodiments, elevated and/or high sCD28 levels are levels at and/or above 5, 6, 7, 8, 9, 10, 12, 14, 15, 17, 20, 25, 30, 35, 40, 50, 60, 70, 80, 90 or 100 ng/mL. Each possibility represents a separate embodiment of the invention. In some embodiments, the cancer comprises high sCD28 levels. In some embodiments, elevated and/or high sCD28 levels are levels at and/or above 5, 10, 15, 20, 25, 30, 35, 40, 45, 50, 55, 60, 65, 70, 75, 80, 85, 90, 95, 100, 150, 200, 300, 400, 500, 600, 700, 800, 900, or 1000% of the levels in a healthy subject. Each possibility represents a separate embodiment of the invention. In some embodiments, the cancer is not breast cancer. In some embodiments, the cancer is selected from melanoma, urothelial carcinoma, head and neck, non-small cell lung cancer, ovarian, kidney, gastric and colorectal. In some embodiments, the cancer is selected from melanoma, urothelial carcinoma, head and neck, non-small cell lung cancer, ovarian, and colorectal. In some embodiments, the cancer is melanoma, urothelial carcinoma, head and neck, non-small cell lung cancer, ovarian, kidney, gastric or colorectal. Each possibility represents a separate embodiment of the invention.

In some embodiments, the method is performed in vivo. In some embodiments, the method is performed in vitro. In some embodiments, the method is performed ex vivo. In some embodiments, the decreasing is performed in vivo. In some embodiments, the decreasing is performed in vitro. In some embodiments, the decreasing is performed ex vivo.

By another aspect, there is provided a method for making an unsuitable subject suitable to receive anti-PD-1 and/or PD-L1 immunotherapy and/or CD80 and/or CD86 based immunotherapy, the method comprising administering an MMP-2 inhibitor, MMP-13 inhibitor or both to the unsuitable subject, thereby making them suitable.

By another aspect, there is provided use of an MMP-2 inhibitor, an MMP-13 inhibitor or both for making an unsuitable subject suitable to receive anti-PD-1 and/or PD-L1 immunotherapy and/or CD80 and/or CD86 based immunotherapy.

In some embodiments, the method further comprises making the unsuitable subject suitable by performing a method of the invention.

In some embodiments, the subject is unsuitable to receive anti-PD-1 and/or PD-L1 immunotherapy. In some embodiments, the subject is unsuitable to receive CD80 and/or CD86 based immunotherapy. In some embodiments, the method is a method of making the subject suitable to receive anti-PD-1 and/or PD-L1 immunotherapy. In some embodiments, the method is a method of making the subject suitable to receive CD80 and/or CD86 based immunotherapy.

In some embodiments, an unsuitable subject has elevated sCD28 levels. In some embodiments an elevated level is elevated above a level in a healthy subject. In some embodiments an elevated level is elevated above a level in a predetermined threshold. In some embodiments, an elevated level is sCD28 level above 5, 10, 15, 20, 25, 30, 35, 40, 45, or 50 ng/mL. Each possibility represents a separate embodiment of the invention. In some embodiments, a sCD28 level above 5, 10, 15, 20, 25, 30, 35, 40, 45, or 50 ng/mL indicates the subject is unsuitable to be treated. Each possibility represents a separate embodiment of the invention. In some embodiments, a sCD28 level above 10 ng/mL indicates the subject is unsuitable to be treated. In some embodiments, a sCD28 level above 20 ng/mL indicates the subject is unsuitable to be treated.

CD80 and CD86 immunotherapies are well known in the art and comprise administering CD80/CD86 and or mimic, derivatives or mimetics thereof to stimulate an immune response. CD80-Fc is currently in clinical trials as an anticancer immunotherapeutic for non-limiting example.

In some embodiments, a level of sCD28 above a predetermined threshold indicates the subject is suitable for treatment with a method of the invention. In some embodiments, a level of sCD28 above a predetermined threshold indicates the subject is suitable for combined immunotherapy and a method of the invention.

In some embodiments, the subject suffers from cancer. In some embodiments, the subject is at risk for developing cancer.

By another aspect, there is provided a method for producing an agent for the performance of a method of the invention, the method comprising:

a. obtaining an agent that binds to a CD28 extracellular domain or fragment thereof; and b. testing an ability of the agent to block cleavage of mCD28 by MMP-2, MMP-13 or both, and selecting at least one agent that blocks cleavage of mCD28 by MMP-2, MMP-13 or both;

thereby producing an agent of the invention.

By another aspect, there is provided a method for producing an agent of the invention, the method comprising:

culturing a host cell comprising one or more vectors comprising a nucleic acid sequence encoding an agent, wherein the nucleic acid sequence is that of an agent that was selected by:

i. obtaining an agent that binds to a CD28 extracellular domain or fragment thereof;

ii. testing an ability of the agent to block cleavage of mCD28 by MMP-2, MMP-13 or both; and iii. selecting at least one agent that blocks cleavage of mCD28 by MMP-2, MMP-13 or both;

thereby producing an agent of the invention.

In some embodiments, the agent is an anti-cleavage agent. In some embodiments, the agent is an anti-shedding agent. In some embodiments, the agent decreases shedding of sCD28 in a subject. In some embodiments, the agent decreases cleavage of mCD28. In some embodiments, the agent decreases cleavage of mCD28 in a subject.

In some embodiments, testing is testing an ability of the agent to block cleavage of mCD28 by MMP-2. In some embodiments, testing is testing an ability of the agent to block cleavage of mCD28 by MMP-13 In some embodiments, testing is testing an ability of the agent to block cleavage of mCD28 by both MMP-2 and MMP-13. In some embodiments, selecting is selecting at least one agent that blocks cleavage of mCD28 by MMP-2. In some embodiments, selecting is selecting at least one agent that blocks cleavage of mCD28 by MMP-13. In some embodiments, selecting is selecting at least one agent that blocks cleavage of mCD28 by both MMP-2 and MMP-13.

In some embodiments, cleavage by MMP-2 is in the stalk domain. In some embodiments, cleavage by MMP-2 is at an MMP-2 cleavage motif. In some embodiments, the cleavage motif is PXX/X (SEQ ID NO: 14) wherein the last X is a hydrophobic residue. In some embodiments, the cleavage motif in CD28 is PSP/L. In some embodiments, cleavage by MMP-2 is between P144 and L145. In some embodiments P144 and L145 are of SEQ ID NO: 1. In some embodiments, cleavage by MMP-2 is between P129 and L130 of SEQ ID NO: 2.

In some embodiments, cleavage by MMP-13 is in the stalk domain. In some embodiments, cleavage by MMP-13 is at an MMP-13 cleavage motif. In some embodiments, the cleavage motif is PXX/X (SEQ ID NO: 14) wherein the last X is a hydrophobic residue. In some embodiments, the cleavage motif in CD28 is PSP/L. In some embodiments, cleavage by MMP-13 is between P144 and L145. In some embodiments P144 and L145 are of SEQ ID NO: 1. In some embodiments, cleavage by MMP-13 is between P129 and L130 of SEQ ID NO: 2.

As used herein, the term "extracellular domain of CD28" refers to the N-terminal portion of CD28 that comes before the transmembrane domain. In some embodiments, an extracellular domain of CD28 is sCD28. In some embodiments, an extracellular domain of CD28 is the CD28 stalk domain. In some embodiments, an extracellular domain of CD28 comprises the stalk domain of CD28. In some embodiments, an extracellular domain of CD28 comprises or consists of the sequence NKILVKQSPMLVAYDNAVNLSCKYSYN-LFSREFRASLHKGLDSAVEVCVVYGNYSQQ LQVYSKTGFNCDGKLGNESVTFYLQNLY-VNQTDIYFCKIEVMYPPPYLDNEKSNGTIIH VKGKHLCPSPLFPGPSKP (SEQ ID NO: 11). In some embodiments, the extracellular domain of CD28 or a fragment thereof is dimeric. In some embodiments, the extracellular domain of CD28 or a fragment thereof is monomeric. In some embodiments, the extracellular domain of CD28 or a fragment thereof is dimeric or monomeric.

As used herein, a "fragment" refers to a partial polypeptide that makes up part of the larger protein or protein domain. In some embodiments, a fragment comprises at least 10, 20, 30, 40 or 50 amino acids. Each possibility represents a separate embodiment of the invention. In some embodiments, a fragment comprises at most 10, 20, 30, 40, 50, 60 70, 80, 90 or 100 amino acids. Each possibility represents a separate embodiment of the invention. In some embodiments, obtaining an agent that binds a fragment of the extracellular domain of CD28 is obtaining an agent that binds specifically to a CD28 stalk domain. In some embodiments, binding a CD28 extracellular domain is specific binding of a CD28 extracellular domain. In some embodiments, specific binding is binding of CD28 and not any other targets. In some embodiments, specific binding is binding of CD28 and not substantially binding any other targets. In some embodiments, specific binding is binding CD28 and not blocking cleavage of any other targets.

In some embodiments, the method further comprises assaying mCD28 downstream signaling in the presence of the obtained agent and selecting at least one agent that neither substantially agonizes nor substantially antagonizes mCD28 signaling. In some embodiments, the selecting is selecting at least one agent that does not antagonize mCD28 signaling. It will be understood by a skilled artisan that for cancer treatment agonizing CD28 signaling might not be deleterious, but that antagonizing the signaling would be counterproductive.

In some embodiments, the method further comprises assaying binding to mCD28 on a surface of a cell and selecting at least one agent that binds to mCD28 on a cell surface. In some embodiments, cell surface binding is assayed. In some embodiments, cell surface binding is not binding to a soluble peptide.

In some embodiments, testing an agent's ability to block cleavage comprises mixing of the agent, the protease and an extracellular domain of CD28 or a fragment thereof comprising a cleavage site. In some embodiments, the testing further comprises sequencing the extracellular domain of CD28 or a fragment thereof to check for truncation and/or cleavage. In some embodiments, the testing further comprises running the extracellular domain of CD28 or a fragment thereof on a gel that is sufficiently sensitive to measure the size change due to cleavage. In some embodiments, the testing further comprises measuring the production of sCD28 from cells expressing mCD28 in the presence of the agent and the protease.

In some embodiments, the method further comprises isolating and/or extracting the agent from the host cell. In some embodiments, the method further comprises isolating and/or extracting the agent from the culture media of the host cell. In some embodiments, the method further comprises purifying the agent from the host cell or the culture media of the host cell.

In some embodiments, obtaining the agent comprises immunizing an organism with the CD28 extracellular domain or fragment thereof, and collecting antibodies from the immunized organism. In some embodiments, the organism is a mouse. In some embodiments, the organism is selected from a rabbit, a mouse, a rat, a shark, a camelid, a chicken, a goat and a phage. In some embodiments, the camelid is selected from a camel, an alpaca and a llama. In some embodiments, the collecting comprises drawing blood. In some embodiments, the collecting comprises:

a. extracting B cells from a spleen of the immunized organism;

b. fusing the extracted B cells with myeloma cells to produce a hybridoma; and c. collecting antibodies from the hybridoma.

In some embodiments, obtaining the agent comprises screening a library of agents for binding to a CD28 extracellular domain or fragment thereof and selecting an agent that so binds. In some embodiments, the library is a phage display library. In some embodiments, the library is an immunized library derived from splenic B cells. In some embodiments, the library is an IgG library. In some embodiments, the library is a Fab library. In some embodiments, the library is a library of VHH antibodies. In some embodiments, the library is a library of single chain, single domain or nanobodies. In some embodiments, obtaining the agent comprises sequencing the agent. In some embodiments, obtaining the agent comprises producing a recombinant form of the agent. In some embodiments, selecting the agent comprises sequencing the agent. In some embodiments, selecting the agent comprises producing a recombinant form of the agent. In some embodiments, the recombinant form is produced from the sequence of the agent. In some embodiments, the method further comprises humanizing the agent.

Expressing a nucleic acid molecule that encodes an agent within a cell is well known to one skilled in the art. It can be carried out by, among many methods, transfection, viral infection, or direct alteration of the cell's genome. In some embodiments, the gene is in an expression vector such as plasmid or viral vector. One such example of an expression vector containing p16-Ink4a is the mammalian expression vector pCMV p16 INK4A available from Addgene.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the nucleic acid sequence encoding an agent is operably linked to a promoter. The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

By another aspect, there is provided an agent produced by a method of the invention.

By another aspect, there is provided a pharmaceutical composition comprising an agent produced by a method of the invention and a pharmaceutically acceptable carrier, excipient or adjuvant. In some embodiments, the administering is administering a pharmaceutical composition of the invention.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

By another aspect, there is provided a kit comprising at least one agent produced by a method of the invention, or the pharmaceutical composition of the invention.

In some embodiments, the kit further comprises a PD-1 and/or PD-L1 based immunotherapeutic. In some embodiments, the kit comprises a label stating the agent produced by a method of the invention is for use with a PD-1 and/or PD-L1 based immunotherapeutic. In some embodiments, the kit comprises a label stating the PD-1 and/or PD-L1 based therapeutic is for use with an agent or pharmaceutical composition produced by a method of the invention.

In some embodiments, the kit further comprises a detection molecule for detecting an agent of the invention. In some embodiments, the detection molecule is a secondary detection molecule. In some embodiments, the detection molecule binds to the agent. Detection molecules are well known in the art, and include, but are not limited to fluorescent moieties and molecule, dyes, and secondary antibodies.

By another aspect, there is provided a kit comprising a PD-1 and/or PD-L1 based immunotherapeutic comprising a label stating it is for use with an agent or pharmaceutical composition produced by a method of the invention.

In some embodiments, a kit of the invention is for use in treating cancer. In some embodiments, a kit of the invention is a diagnostic kit. In some embodiments, a kit of the invention is for use in determining serum levels of sCD28 in a subject in need thereof. In some embodiments, the subject suffers from cancer. In some embodiments, a kit of the invention is for use in determining suitability of a subject to be treated with an agent or pharmaceutical composition of the invention. In some embodiments, the kit is for use in determining suitability of a subject to be treated with anti-PD-1/PD-L1 based immunotherapy.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Matrix Metalloproteinases and ADAM's—Commercial recombinant human metalloproteinases MMP-1 (Cat. No. AS-55575), MMP-9 (Cat. No. AS-55576), MMP-10 (Cat. No. AS-72067), MMP-12 (Cat. No. AS-55525) and MMP-13 (Cat. No. AS-72257) are from AnaSpec. Recombinant human ADAM-10 (Cat. No. 936-AD) and ADAM-17 (Cat. No. 930-ADB) were purchased from R&D system. Recombinant human MMP-2 was used both from Anaspec (Cat. No. AS-72005) and R&D system (Cat. No. 902-MP). Pro-MMP-2 and pro-MMP-10 were activated with 1 mM p-aminophenylmercuric acetate (APMA) for 1 hr at 37° C. according to manufacturer protocol.

Protease Inhibitors—Protease inhibitors were added at the indicated concentration at the start of each experiment. In cellular week long assays another portion of the inhibitors was added after 3 days at the final concentration. The protease inhibitor used is ARP-100 (Tocris, Cat. No. 2621).

Synthetic Quenched Peptides—Fluorogenic substrate corresponding to the amino acid sequence of human CD28 stalk region, 4-(4-dimethylaminophenyl) diazenylbenzoic acid (DABCYL)—KGKHLSPSPLFPGPSKP-Glu-5-((2-amino-ethyl) amino) naphthalene-1-sulfonic acid (EDANS)-NH$_2$, was custom synthesized by Gencust Europe. Cysteine residue at position 141 was mutated to Serine due to a solubility problem.

Fluorogenic Assay—The assay was performed with indicated MMP's (10 or 30 ng) in 50 mM Tris, 10 mM CaCl$_2$), 150 mM NaCl, 0.05% Brij-35, pH 7.5 or ADAM10/ADAM17 (5 µg/mL) in 25 mM Tris, 2.5 mM ZnCl$_2$ and 0.005% Brij-35, pH 9. Cleavage of the fluorogenic substrate (10 µM) was measured at Ex340/Em490 nm using Biotek Synergy H1 spectrofluorometer.

MALDI-TOF-mass spectrometry analysis—Mass analyses were carried out on an AutoFlex Speed I mass spectrometer (Bruker Daltonics). Samples were diluted in a solution of 2,5-dihydroxybenzoic acid (DHB) and acetonitrile. Mass spectra were acquired in the reflectron negative mode in the 500-2500 mass-to-charge ratio (m/z) range. MALDI-TOF-mass spectrometry spectra were processed using FlexAnalysis software from Bruker Daltonics.

ELISA—Commercial ELISA kits were used for quantitation of the amount of soluble human CD28 (R&D, Cat. No. DY342). Cell proliferation and viability (MTT assay) was conducted according to manufacturer instructions (Roche, Cat. No. 11465007001).

Isolation of human immune cells—PBMCs were isolated from fresh blood samples of healthy donors using standard lymphocytes separation medium (MBP, Cat. No. 850494). All cells were grown in complete RPMI-1640 media supplemented with 10% HI-FCS and pen/strep mixture.

SEB or CMV activation of PBMCs for the generation of soluble CD28—0.1×10$^6$ PBMCs were stimulated with 0.5 ng/mL SEB (Sigma, Cat. No. 54881) for 7 days at 37° C. with/without the indicated concentration of various protease inhibitors in 96 well plate. For CMV stimulation 0.5×10$^6$ PBMCs were stimulated with 0.5 µg/mL CMV peptivator (Milteny Biotec, Cat. No. 130-093-435) for 7 days at 37° C. with/without the indicated concentration of various protease inhibitors in a 96 well plate.

Synthetic Biotinylated and Myc tagged Peptides—Substrate peptide with the final form of "EQKLISEED-LGGGGHVKGKHLCPSPLFPGPSKP (SEQ ID NO: 17)-biotin" was designed to include the amino acid sequence of human CD28 stalk region (His134-Pro152) between an N-terminal cMyc tag (EQKLISEEDL, SEQ ID NO: 18) followed by four glycine sequence and a C-terminal biotin conjugation. A L145K mutated peptide was synthesized with same design with the sole replacement of the leucine residue at position 145 with a lysine residue (EQKLISEED-LGGGGHVKGKHLCPSPKFPGPSKP, SEQ ID NO: 19). This generates a mutant cleavage site of PSPK (SEQ ID NO: 20). Peptides were custom synthesized by GeneCust Europe. The Cysteine residue at position 141 was used to generate a dimeric peptide by a disulfide linkage.

In-vitro cleavage assay—25 or 50 ng pf purified recombinant MMP-2 or MMP-13 were incubated with 62.5 nM dimeric substrate peptides (WT or L145K mutant). The assay was performed in 50 mM Tris, 10 mM CaCl$_2$, 150 mM NaCl, 0.05% Brij-35, at pH 7.5. After 5 hr of reaction time the mixture was diluted to a final 1 nM concentration of peptide and loaded on a neutravidin plate to bind the peptide. After 1 hr incubation at room-temperature the plate was washed, and detection of uncleaved peptide was done with an anti-cMyc antibody conjugated to HRP (Biolegend, Cat. No. 626802).

Example 1: Human CD28 Undergoes Proteolytic Shedding Mediated by MMP-2

It has previously been shown (International Patent Application WO2019/175885, herein incorporated by reference in its entirety) that broad protease inhibitors such as TAPI can diminish levels of sCD28 produced by chronically stimulated human PBMCs. The effects of this inhibition are dose dependent and demonstrate that immune cells produce sCD28 by active shedding. This was observed both in a Jurkat T cell line and in human CD4 T cells from peripheral blood of healthy donors.

It has been hypothesized that ADAM-10 and ADAM-17 may play a role in this shedding. To directly test active cleavage of the stalk region of human CD28, an in vitro assay was performed in which various recombinant human matrix metalloproteases (MMPs) and disintegrin and metalloproteinase domain containing proteins (ADAMs) were incubated with quenched fluorogenic peptides of the stalk region. Only proteases that are reported to be expressed by T cells were assayed. The sequence of the peptide used was KGKHLSPSPLFPGPSKPE (SEQ ID NO: 16). A Cys141 to serine mutation was made and a glutamic acid residue was added to increase the solubility of the protein and to accommodate conjugation of the fluorophore. The quencher DABCYL was conjugated to the N-terminus and the fluorophore EDANS was conjugated to the C-terminus. When intact, the fluorochrome on the peptide is quenched and no fluorescence is measured. Cleavage of the peptide allows the fluorochrome to dissociate from the quencher and fluorescence is measurable by a dedicated reader. Six MMPs and both ADAM-10 and ADAM-17 were tested. The peptide alone without any sheddase added was used as a control to normalize the readings. As can be clearly seen in FIG. 1A, MMP-2 cleaves the stalk domain peptide, while ADAM-10 and ADAM-17 did not. MMP-13 also cleaves the stalk domain, but at a much lower rate and efficiency than MMP-2. This result is highly unexpected as ADAM-10 and ADAM-17 specific inhibitors had been shown to partially suppress CD28 cleavage. Without being bound to any one theory, it is possible that these proteases play a supporting role in CD28 cleavage or are possibly part of a cascade that results in CD28 cleavage, while not actively cleaving the protein themselves.

Figure 1B:
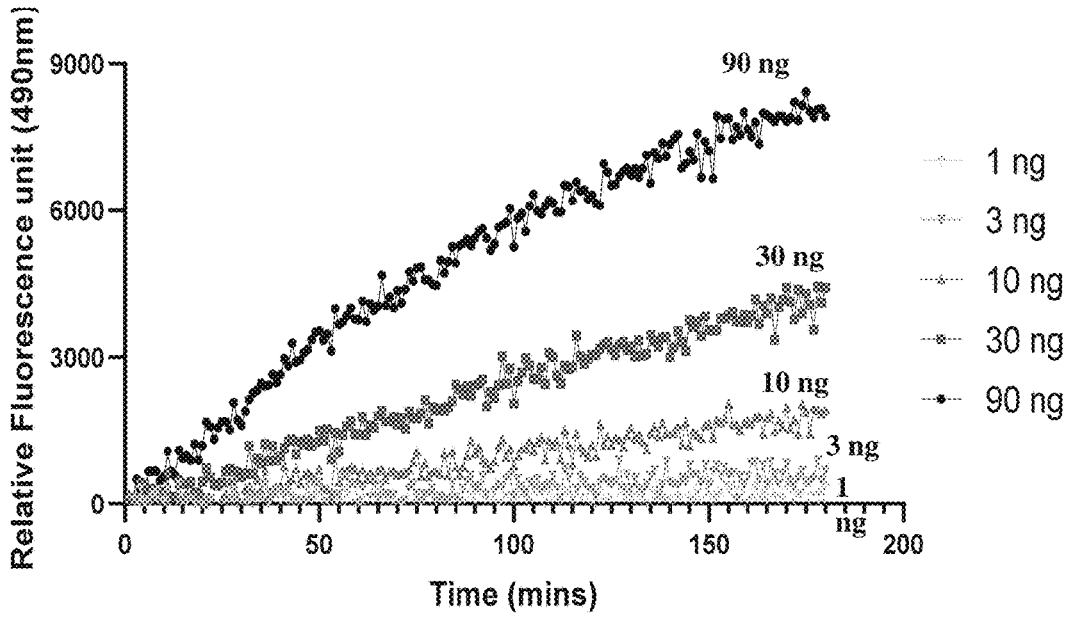
Figure 1C:
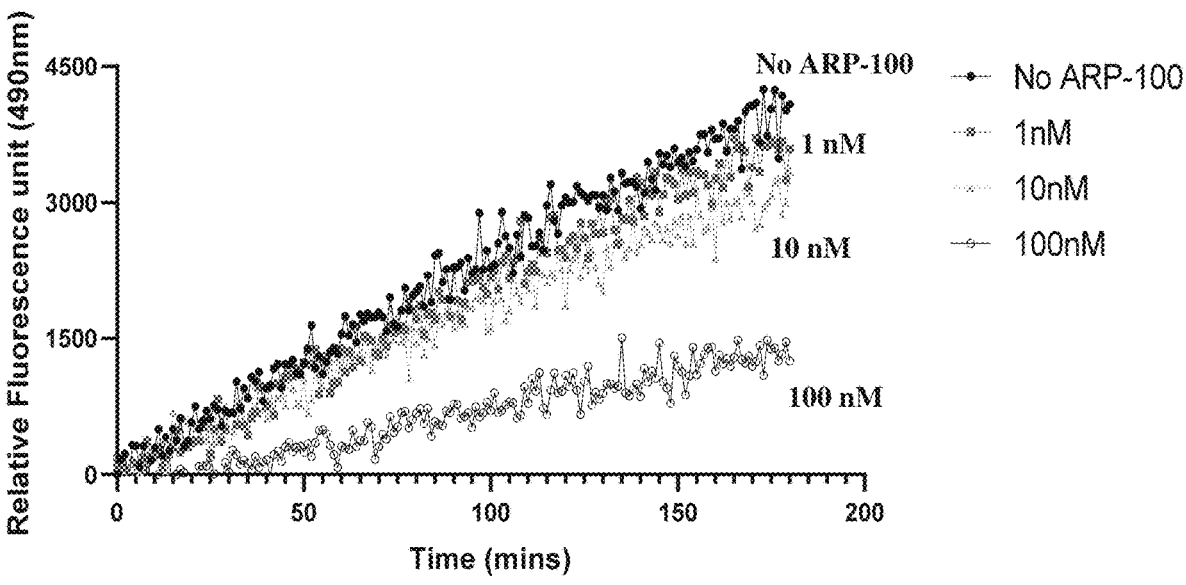

MMP-2's proteolytic effect was further elucidated by titration of the protease to show specific inhibition. Various amounts of MMP-2 were tested, and it was confirmed that the cleavage of the peptide was dose dependent (FIG. 1B). Similarly, it was shown that as the dose of the MMP-2 specific inhibitor ARP-100 was increased, cleavage decreased in a dose dependent manner (FIG. 1C).

Figure 1D:
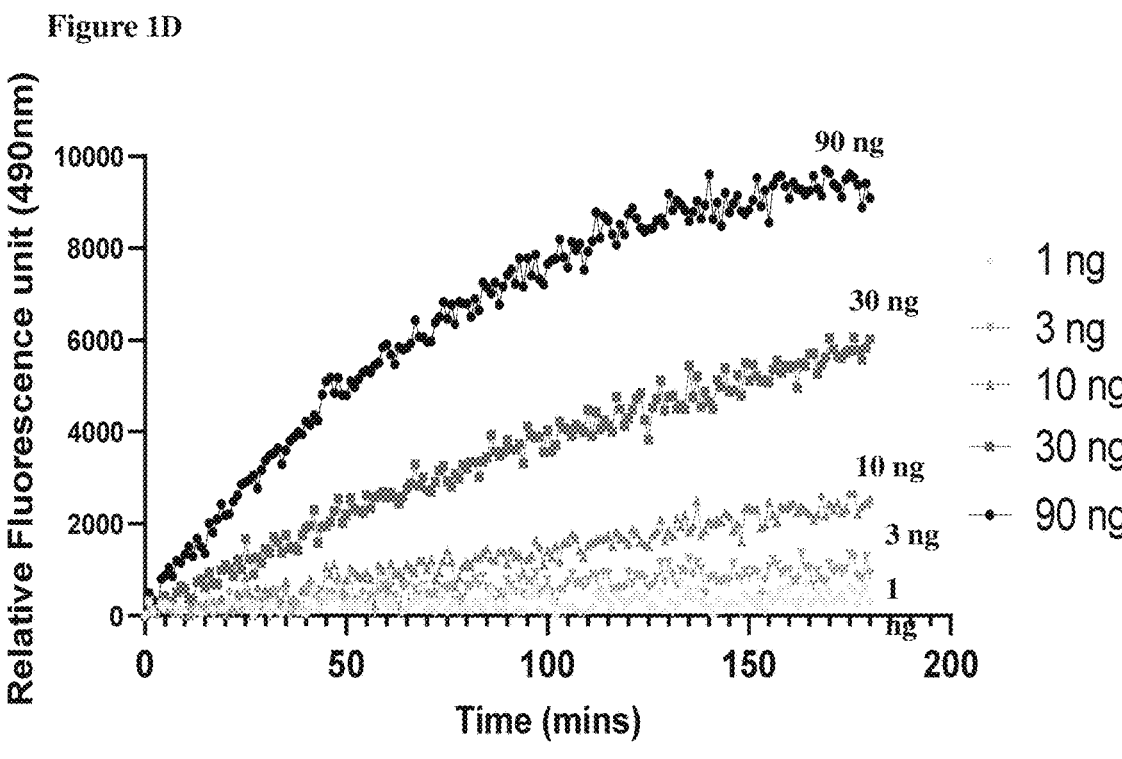
Figure 1E:
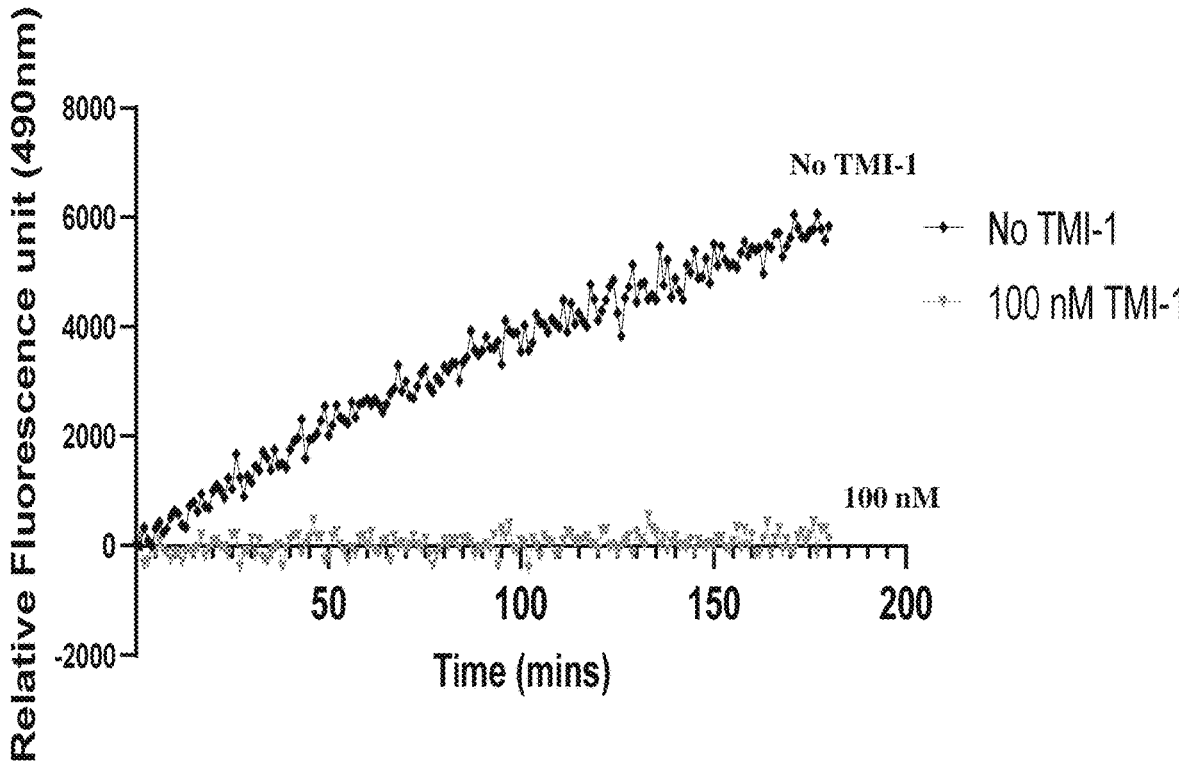

MMP-13's proteolytic effect was also further elucidated by titration of the protease to show specific inhibition. Various amounts of MMP-13 were tested, and it was confirmed that the cleavage of the peptide was dose dependent (FIG. 1D). Similarly, it was shown that as the dose of the broad MMP inhibitor TMI-1 was increased, cleavage decreased in a dose dependent manner (FIG. 1E).

Example 2: MMP-2 Inhibitor Suppresses CD28 Cleavage

Figure 2A:
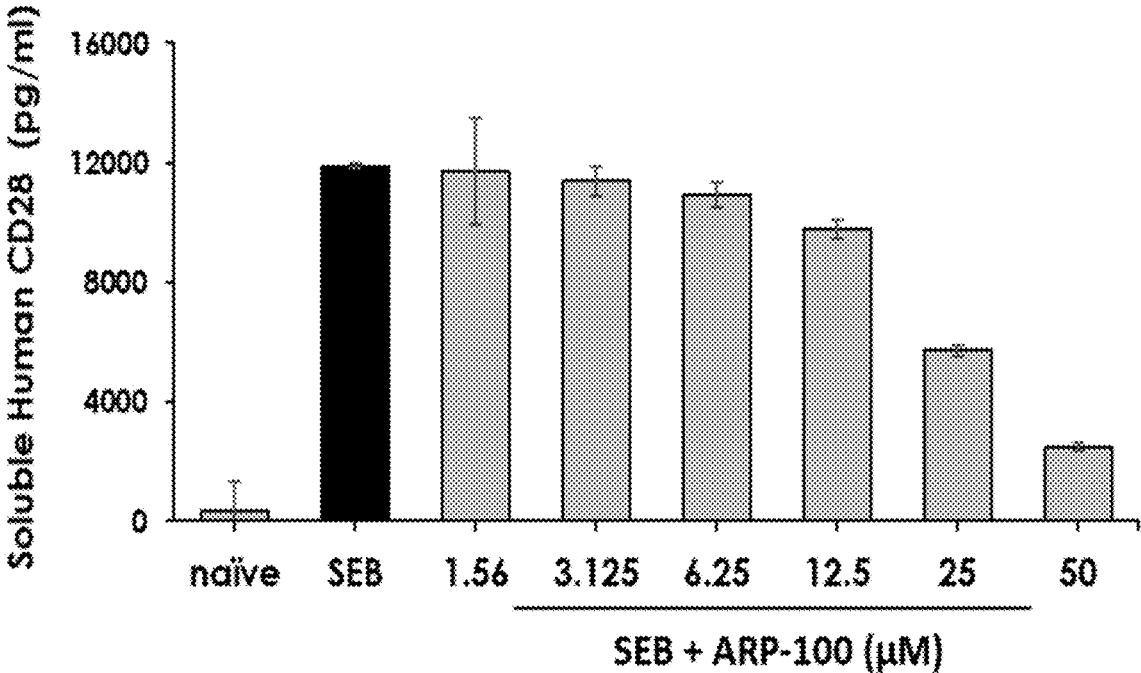
FIGS. 2A-2B. (2A-2B) Bar graphs of sCD28 levels in a culture of (2A) SEB or (2B) CMV stimulated human PBMCs. Varying levels of the MMP-2 inhibitor ARP-100 were added, and unstimulated PBMCs and stimulated PBMCs without addition of the inhibitor were used to show basal levels of soluble CD28.
Figure 2B:
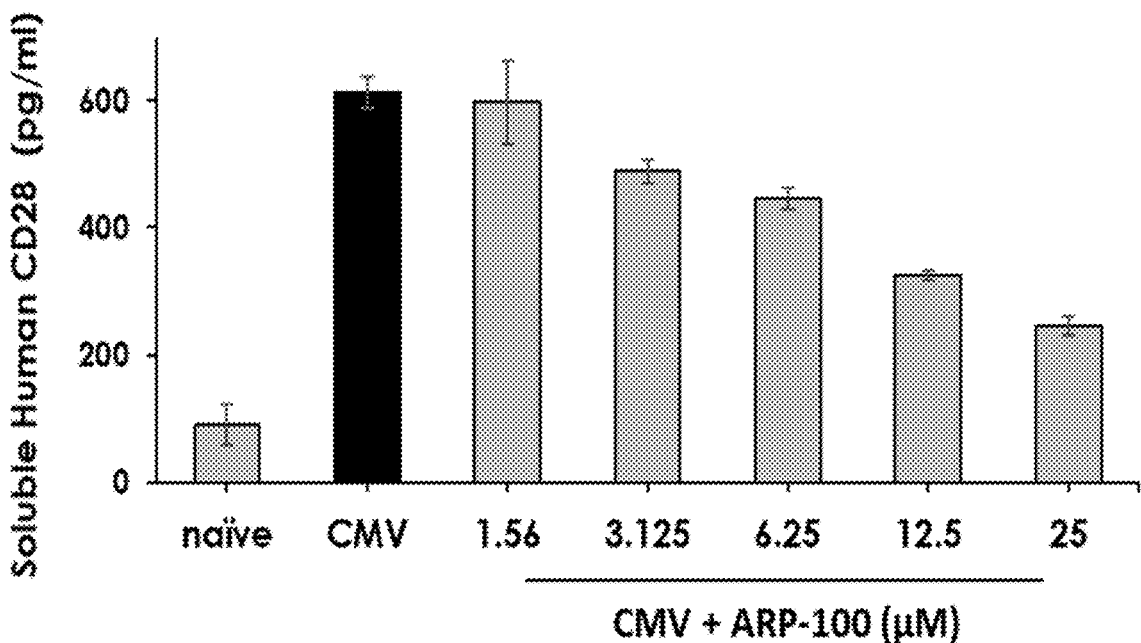

The effect of an MMP-2 specific inhibitor on CD28 cleavage in vivo was tested. PBMCs from healthy human donors were activated with SEB or CMV for six days to stimulate production of sCD28. Dose-dependent inhibition by the MMP-2 specific inhibitor ARP-100 was tested and sCD28 levels were measured by specific ELISA (FIG. 2A-B). These results confirmed that this specific inhibitor is capable of suppressing CD28 cleavage and sCD28 production.

Example 3: The Location of MMP-2/MMP-13 Cleavage within the Stalk Domain

Figure 3A:
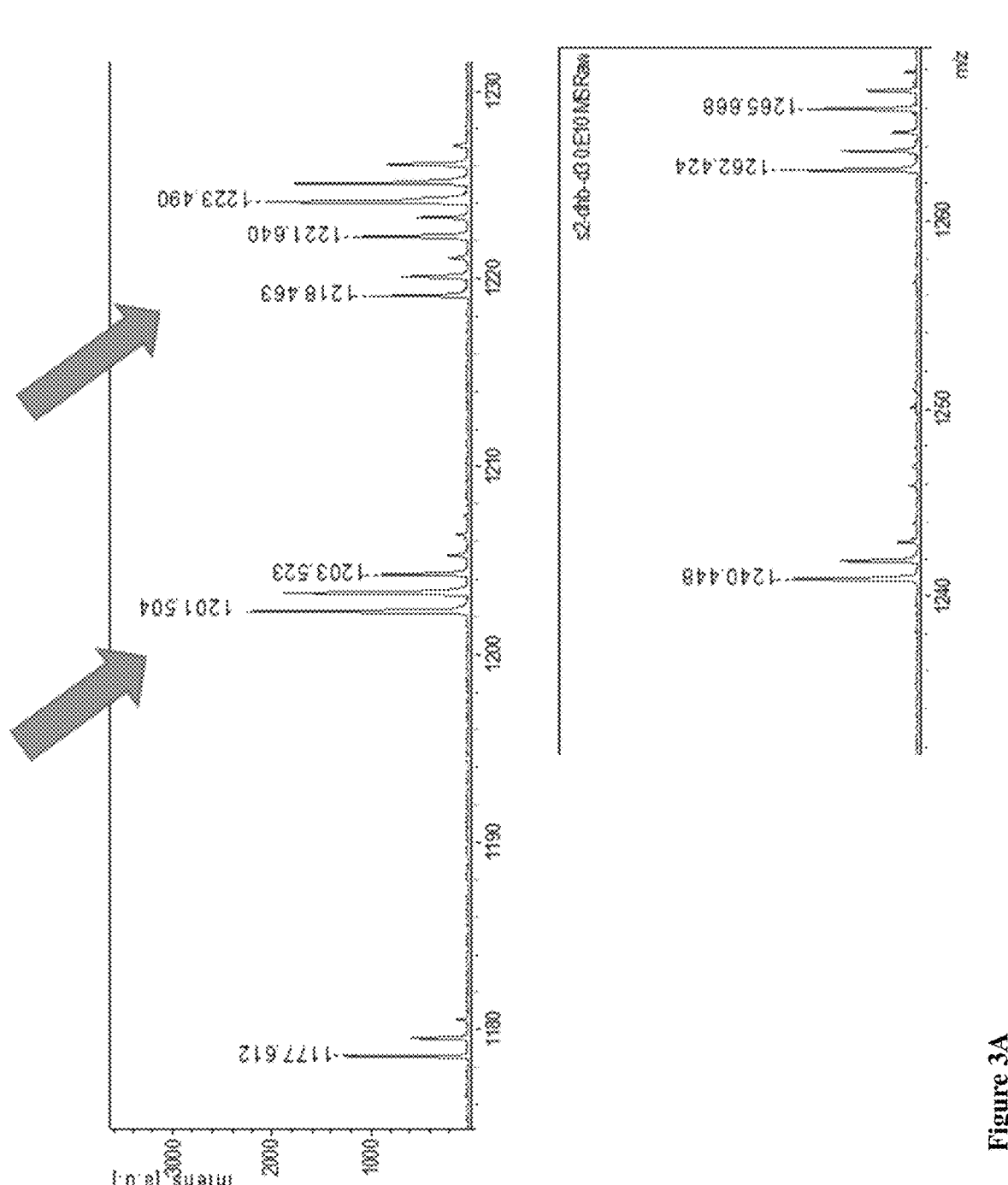
FIGS. 3A-3D. (3A-3C) Spectra of mass spectrometry readouts from (3A) incubation of the stalk peptide with MMP-2, (3B) the stalk peptide alone, and (3C) MMP-2 alone. (3D) The histogram of 3A with an analysis of the relevant peaks and a diagram of the stalk peptide showing the location of cleavage.
Figure 3B:
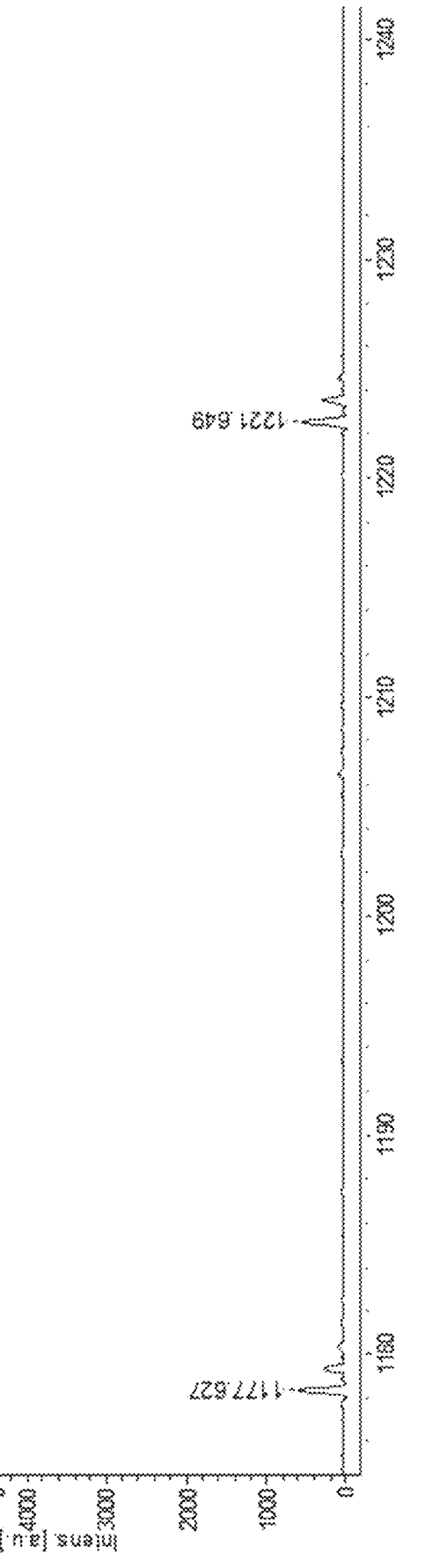
Figures 3B, 3C:
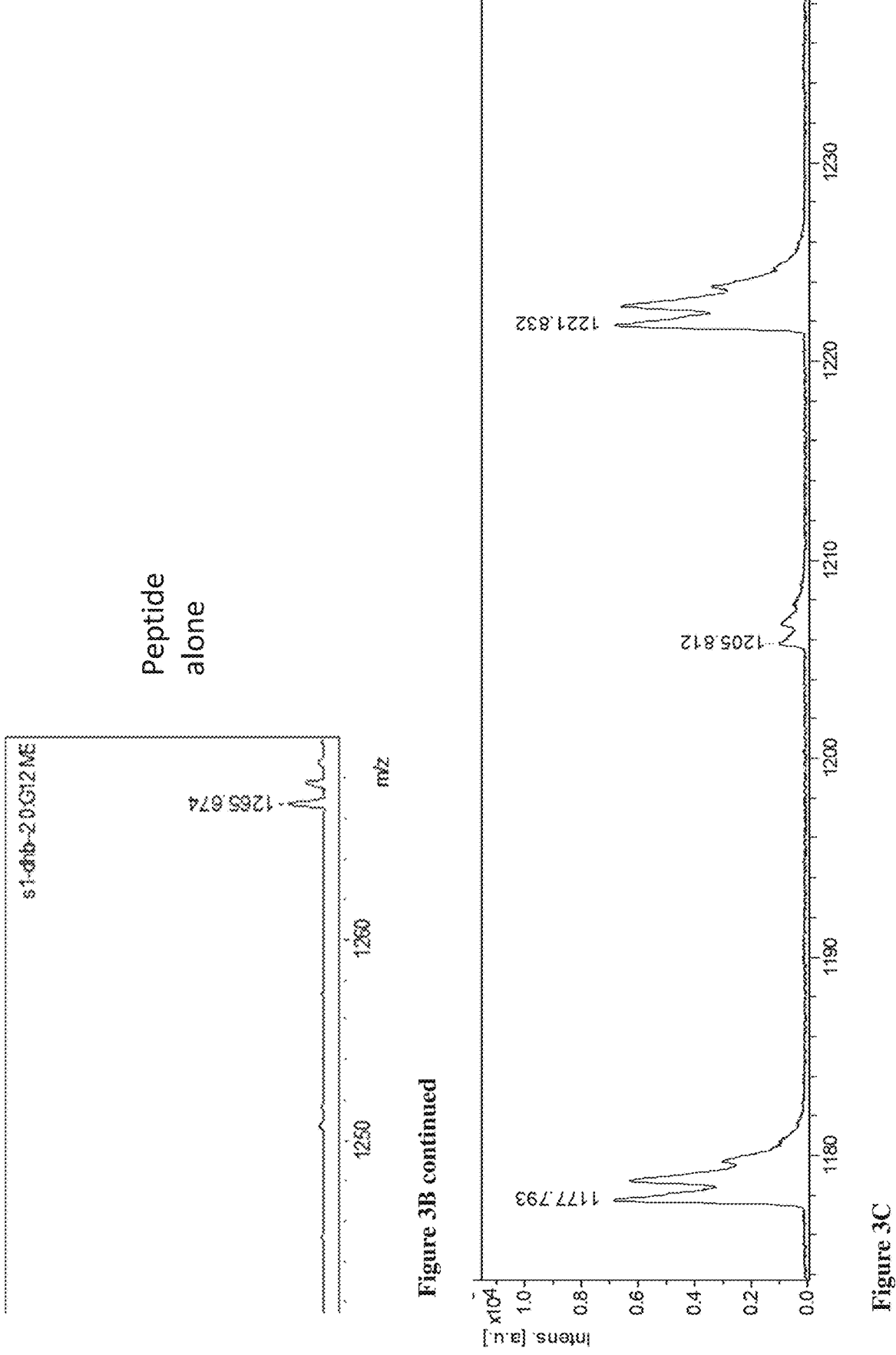
Figure 3C:
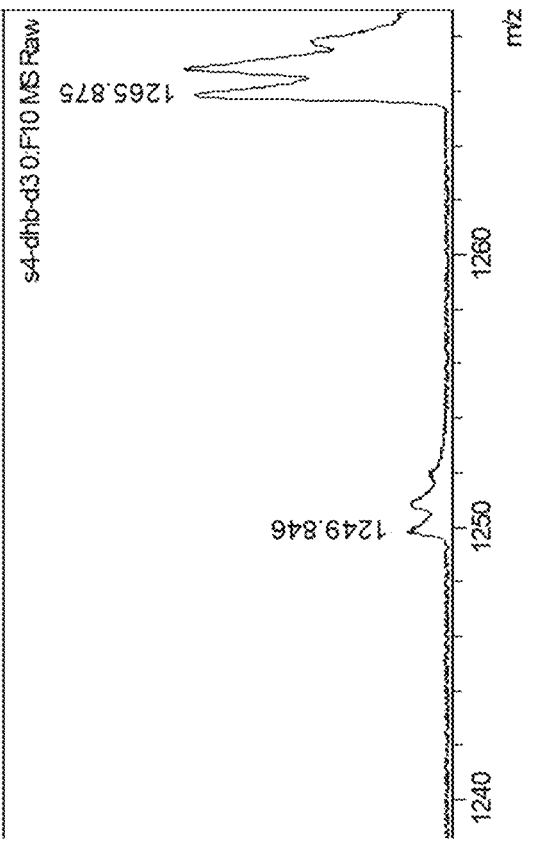
Figure 3D:
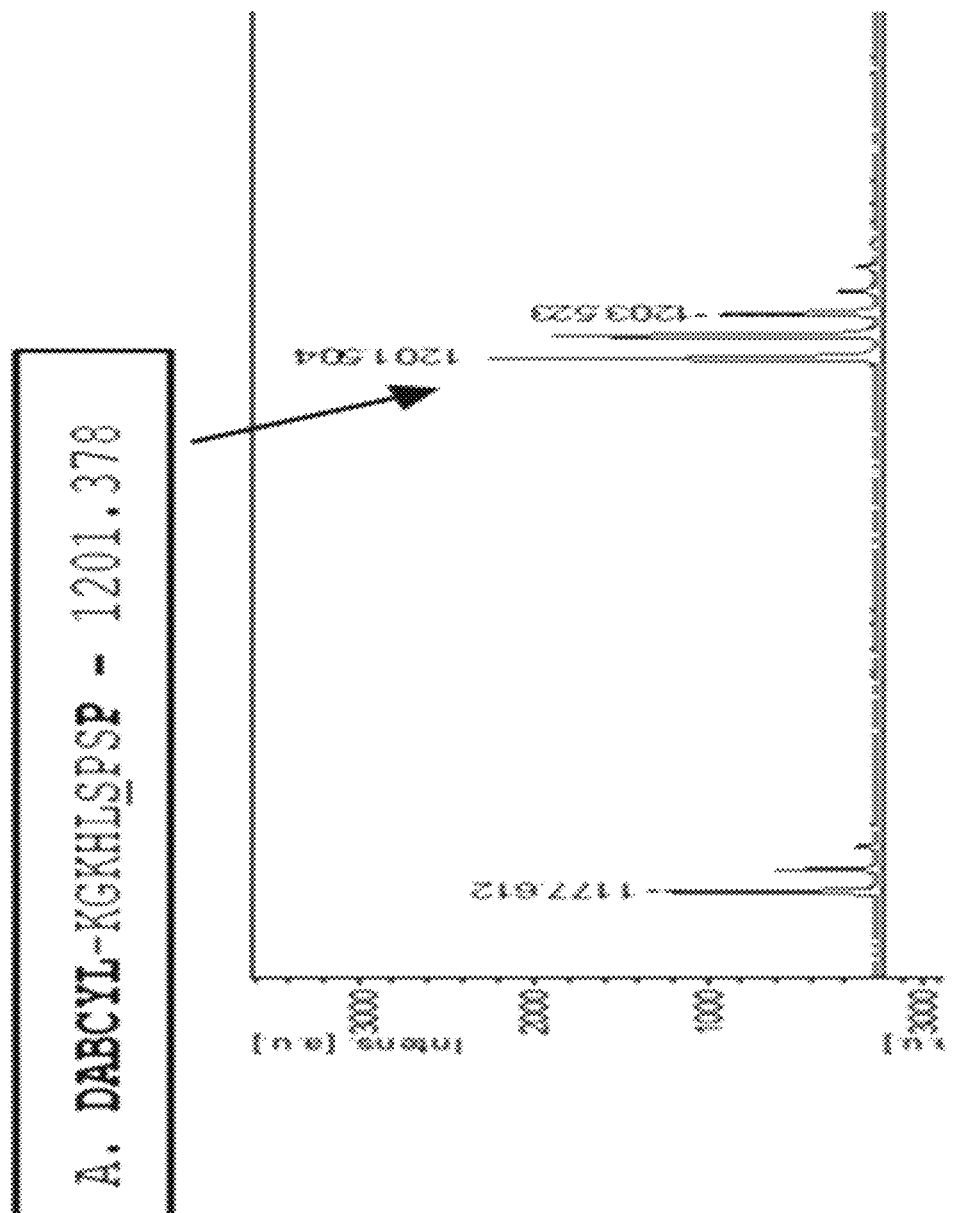
Figure 3D:
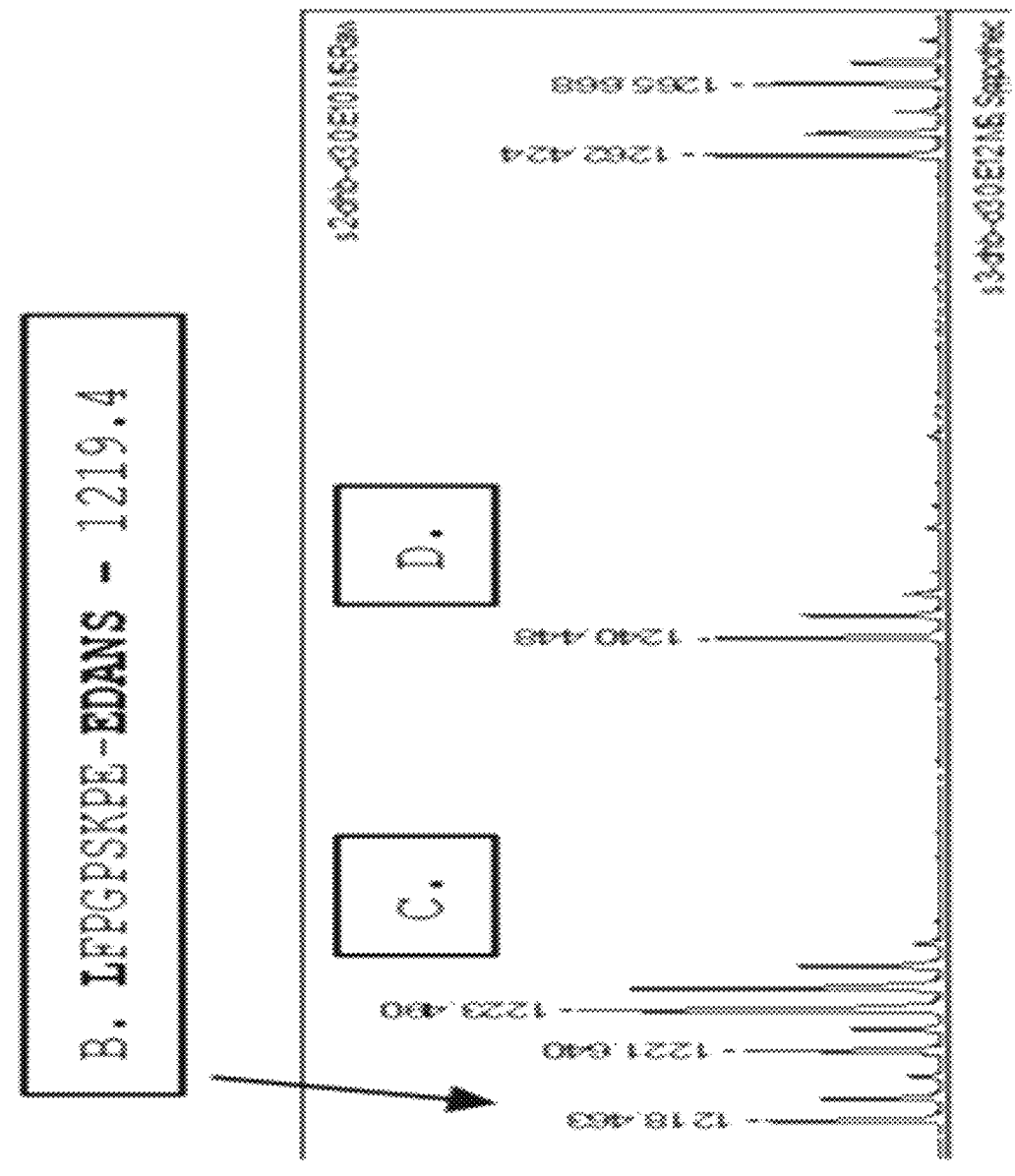

In order to determine the site of MMP-2/MMP-13 cleavage, the stalk domain peptide (SEQ ID NO: 9) was incubated with MMP-2 for five hours and the resultant cleavage products were analyzed by MALDI-TOF mass spectrometry. By comparing the resultant analysis (FIG. 3A) to analysis of the intact peptide (FIG. 3B) and analysis of the MMP-2 enzyme (FIG. 3C) four new peaks were identified which represent the two cleavage products. Analysis of the molecular weights of these two products determined that they were KGKHLSPSP (SEQ ID NO: 12) and LFPGPSKPE (SEQ ID NO: 13). The two additional peaks represented these two cleavage products in association with a sodium ion. This shows that MMP-2 cleaves the stalk domain between the second P of the domain and the second L (FIG. 3D). These residues correspond to proline 144 and leucine 145 of CD28 (see SEQ ID NO:1). The consensus target motif for MMP-2 is $PXX/X_{hydro}$, (SEQ ID NO: 14) wherein the last X is hydrophobic; thus PSP/L (SEQ ID NO: 15) fits as a target for MMP-2.

Figure 4A:
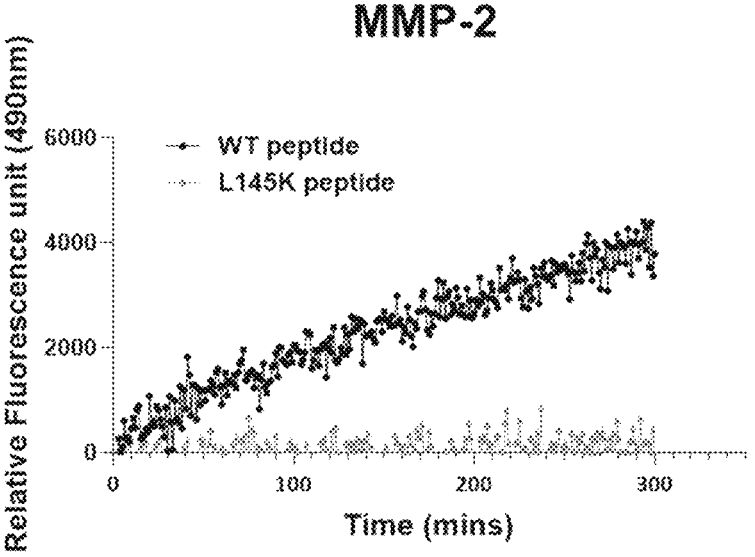
FIGS. 4A-4D. Mutating Leu145 abrogates cleavage of CD28 stalk region. (4A-4B) Line graphs of fluorescence from quenched fluorogenic peptides of WT or L145K CD28 stalk region (2.5 µM), incubated with 30 ng of (4A) MMP-2 or (4B) MMP-13. (4C-4D) Bar charts of the % of intact peptide remaining from WT or L145K biotinylated and myc tagged dimeric peptides of CD28 stalk region (62.5 nM) following incubation with either (4C) rhMMP-2 (25 or 50 ng/reaction or (4D) rhMMP-13 (25 or 50 ng/reaction) for 5 hr. Incubation without each enzyme was used as a control. Remaining peptide was calculated by dividing the signals with enzyme by the signal with peptide alone signal and multiplying by 100.
Figure 4B:
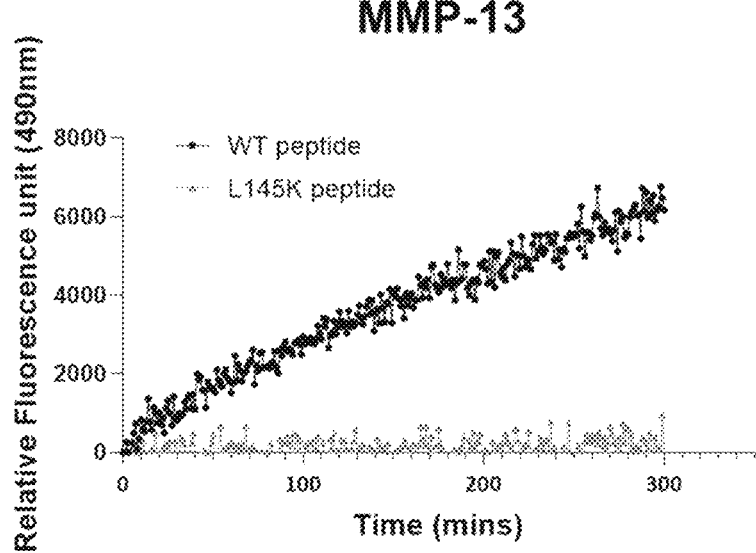

In order to confirm the location of the cleavage site, the fluorogenic peptide was generated with a mutation at L145 that converts the leucine to a lysine. The cleavage site which was identified as PSPL is now abolished as the sequence on the mutant peptide is PSPK. Lysine was specifically selected as it is not hydrophobic. The cleavage assay, as described hereinabove (FIGS. 1B and 1D), was repeated with the WT and mutant peptides (2.5 µM) and 30 ng of MMP-2 (FIG. 4A) or 30 ng of MMP-13 (FIG. 4B). As expected, both enzymes efficiently cleaved the WT peptide, and both were completely incapable of cleaving the mutant peptide.

Figure 4C:
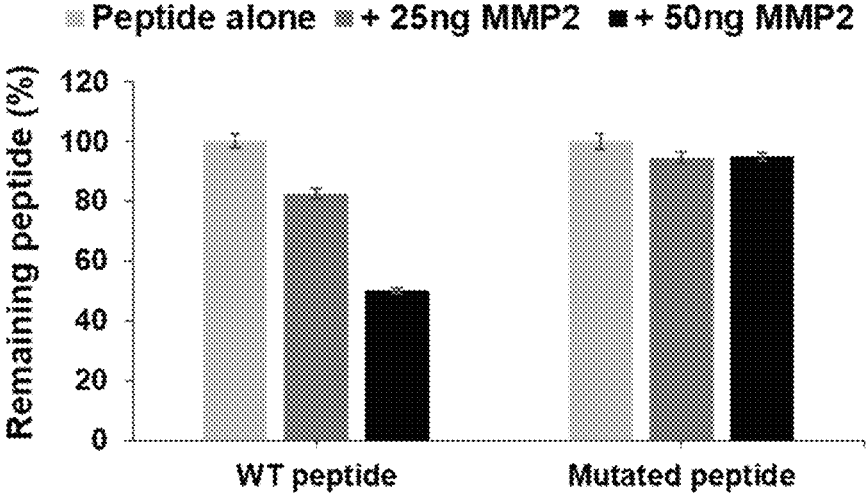
Figure 4D:
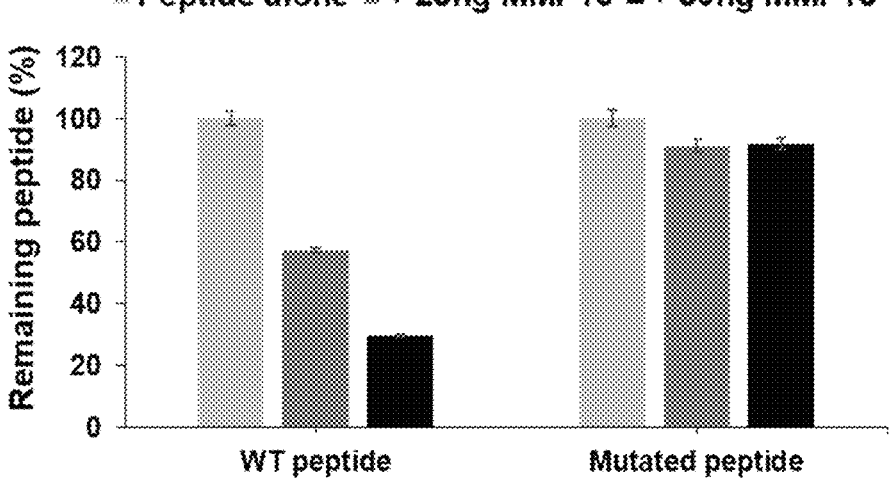

In a further test of the cleavage site, the WT and mutant peptides were generated with an N-terminal Myc tag and a C-terminal biotin tag. These peptides were incubated without enzyme or with two concentrations (25 ng and 50 ng) of MMP-2 (FIG. 4C) or MMP-13 (FIG. 4D). Following a 5-hour incubation, the peptides were loaded on a neutravidin coated plate so as to retain the biotin tagged peptides. Only fully intact peptide was measured using an anti-Myc tag antibody. As expected, the mutated peptide was not substantially cleaved (<5%) by either MMP-2 or MMP-13, while the WT peptide was cleaved in a dose dependent manner. This data taken together confirms that the cleavage site of both MMP-2 and MMP-13 within the CD28 stalk domain is at the PSPL motif.

Example 4: Single-Domain Antibodies Inhibit sCD28 Cleavage by MMP-2 and MMP-13

Small agents capable of binding mCD28 and blocking cleavage by MMP-2 and MMP-13 were designed. Single domain antibodies were isolated using a phage library of naïve llama derived VHH. The library was composed of VHH sequences that were taken from naïve non-immunized Llama, i.e., extracting B cells and sequencing the whole available repertoire of VHH CDRs. These CDRs were implemented into phage to generate a library. Using ELISA and flow cytometry, the library was screened against recombinant CD28 extracellular domain and the dimeric stalk region peptide to find antibodies that specifically bind the stalk region of human CD28. The VHH sequences found to specifically bind the stalk region of human CD28 are: EVQLVESGGGLVQAGESLRLSCAASGSIASI-NAMGWYRQAPGSQRELVAAISGGGDTY YADSVKGRFTISRDNAKTTVYLQMNSLRPED-TAVYYCVVDLYGSDYWDWGQGTQVT VSSAAAH-RHHHHHH (SEQ ID NO: 29, clone 2A1); EVQLVESGG-GLVQAGGSLRLSCAASGSLFSINA MAWYRQAPGKQRELVAAITSSGSTN YANS-VKGRFTVSRDNAKNTMYLQMNSLKPED-TAVYYCVVDEYGSDYWIWGQGTQV TVS-SAAAHHHHH (SEQ ID NO: 30, clone 4A4); and QVQLVESGGGLVQAGGSLRLSCAASGSIFSI-NAMGWYRQAPGKQRERVAAITSGGSTN YADSVKGRFTISRDNAKNTVYLQMNN-LEPRDAGVYYCVVDLYGEDYWIWGQGTQVT VSSAAAHRHHHHHH (SEQ ID NO: 31, clone 4A1). The VHHs were produced as recombinant proteins in CHO cells and then evaluated for cellular binding and anti-shedding activity as described below. A His-tag at the C-terminus was used for purification and was linked via triple alanine repeat. The CDRs of the three investigated clones are provided in Table 1.

TABLE 1

| VHH Clone | CDR1 (SEQ ID) | CDR2 (SEQ ID) | CDR3 (SEQ ID) |
|---|---|---|---|
| 2A1 | INAMG (21) | AISGGGDTYYADS VKG (22) | DLYGSDYW D (23) |
| 4A4 | INAMA (24) | AITSSGSTNYANS VKG (25) | DEYGSDYW I (26) |
| 4A1 | INAMG (21) | AITSGGSTNYADS VKG (27) | DLYGEDYW I (28) |

Figure 5:
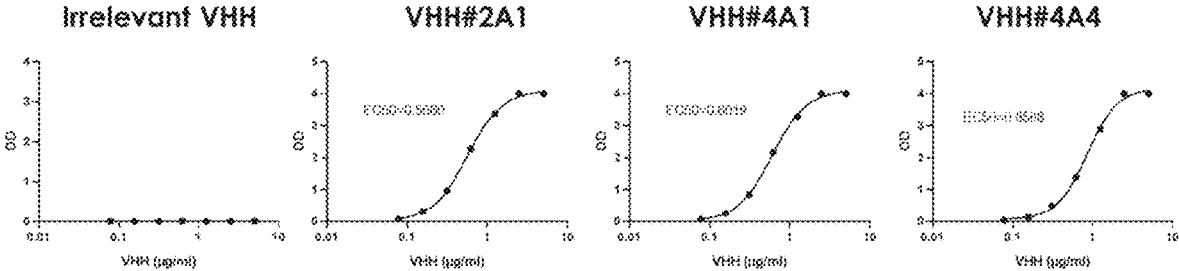
FIG. 5: Binding to Human CD28 stalk region sequence by ELISA. Analysis of antigen binding by serial dilution of different VHH clones. Biotin conjugated CD28 stalk region dimeric peptide serving as antigen was immobilized on neutravidin coated ELISA maxi-sorb plates. Serial dilution of VHH clones was preformed and detection of bound VHH was done with anti His tag-HRP conjugated antibody and development was done with TMB.
Figure 6:
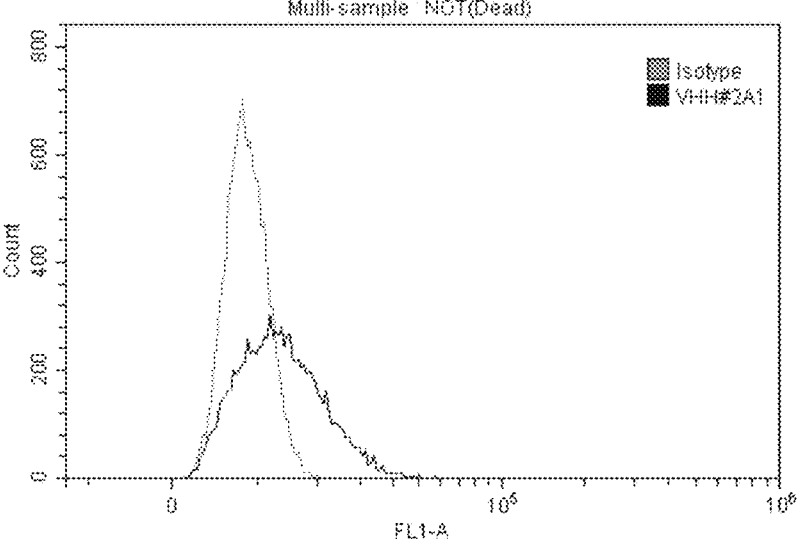
FIG. 6: Binding of VHH #2A1 to membranal human CD28. FITC conjugated VHH clone 2A1 (50 µg/mL, black histogram) and FITC conjugated isotype control (mIgG, 50 µg/mL, grey histogram) were incubated with HEK cells overexpressing human CD28. Binding was evaluated by FACS analysis.
Figure 7:
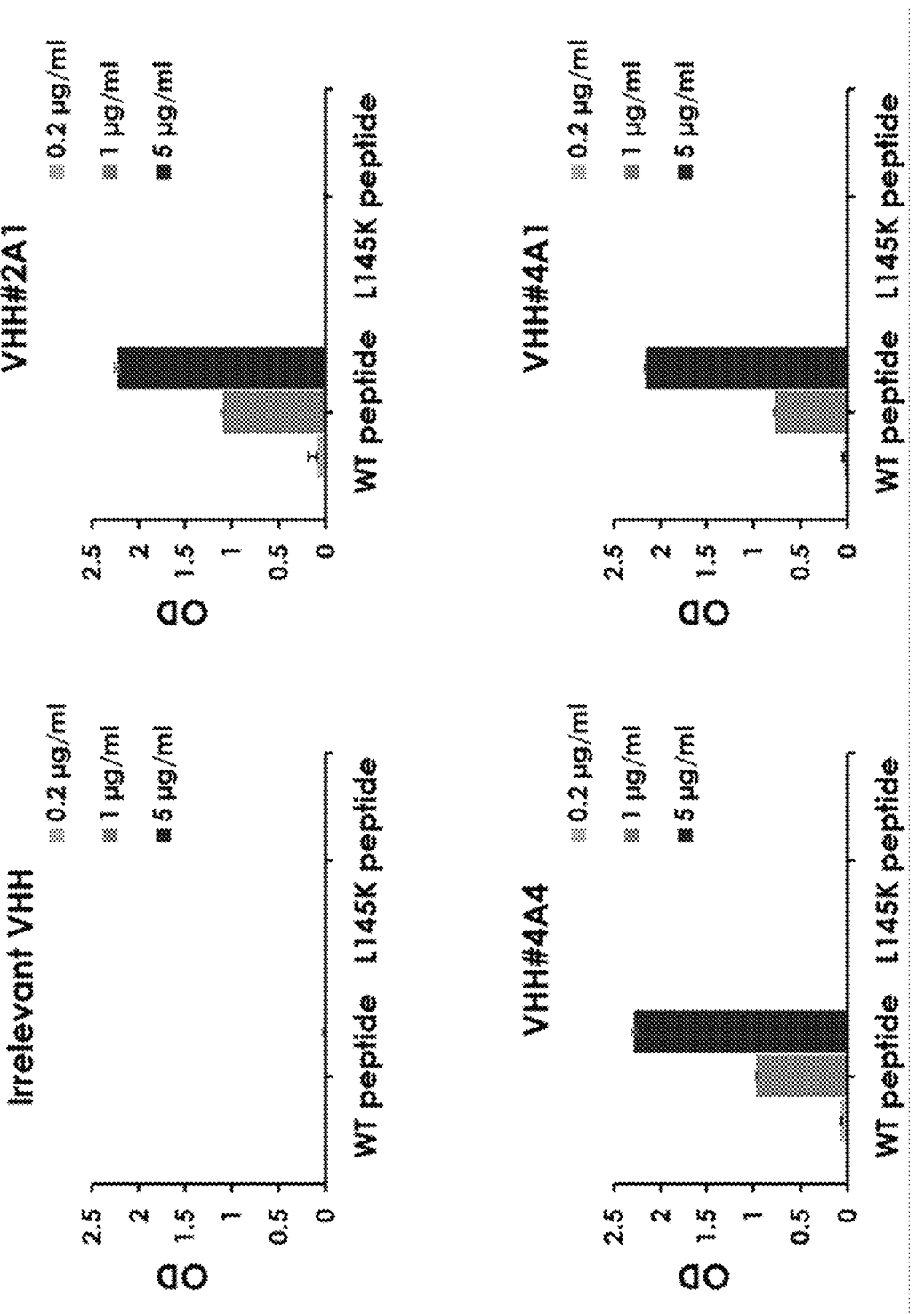
FIG. 7: Anti CD28 stalk region VHH clones 2A1, 4A1 and 4A4 bind specifically to MMP cleavage site of human CD28. Comparison of the specific binding of VHH clones either to human CD28 stalk region WT sequence or to L145K mutated sequence by direct ELISA. Biotin conjugated wild-type or L145K CD28 stalk region dimeric peptides were immobilized on neutravidin coated ELISA maxi-sorb plates. A dilution series of VHH clones (0.2-5 µg/mL) and an irrelevant VHH clone (top left chart) was performed and detection of bound VHH was done with anti His tag-HRP conjugated antibody and development was done with TMB.

Binding of the VHH clones to the human CD28 stalk region sequence was first confirmed with ELISA using serial dilution of VHH clones (FIG. 5). Binding to membranal human CD28 on the cellular level was confirmed with FACS analysis using labeled VHH clone and HEK cells overexpressing CD28 (FIG. 6). Membranal CD28 binding demonstrates access to the CD28 membrane proximal region. Previous experimentation has shown that the size of the agent is critical to access this region, as full-size antibodies that could bind to the CD28 stalk region peptides could not bind to the CD28 stalk region on cells. Notably, VHH clones were not capable of binding human CD28 stalk region sequence with a L-K substitution at amino acid residue 145, located within the MMP cleavage site (FIG. 7).

Figure 8:
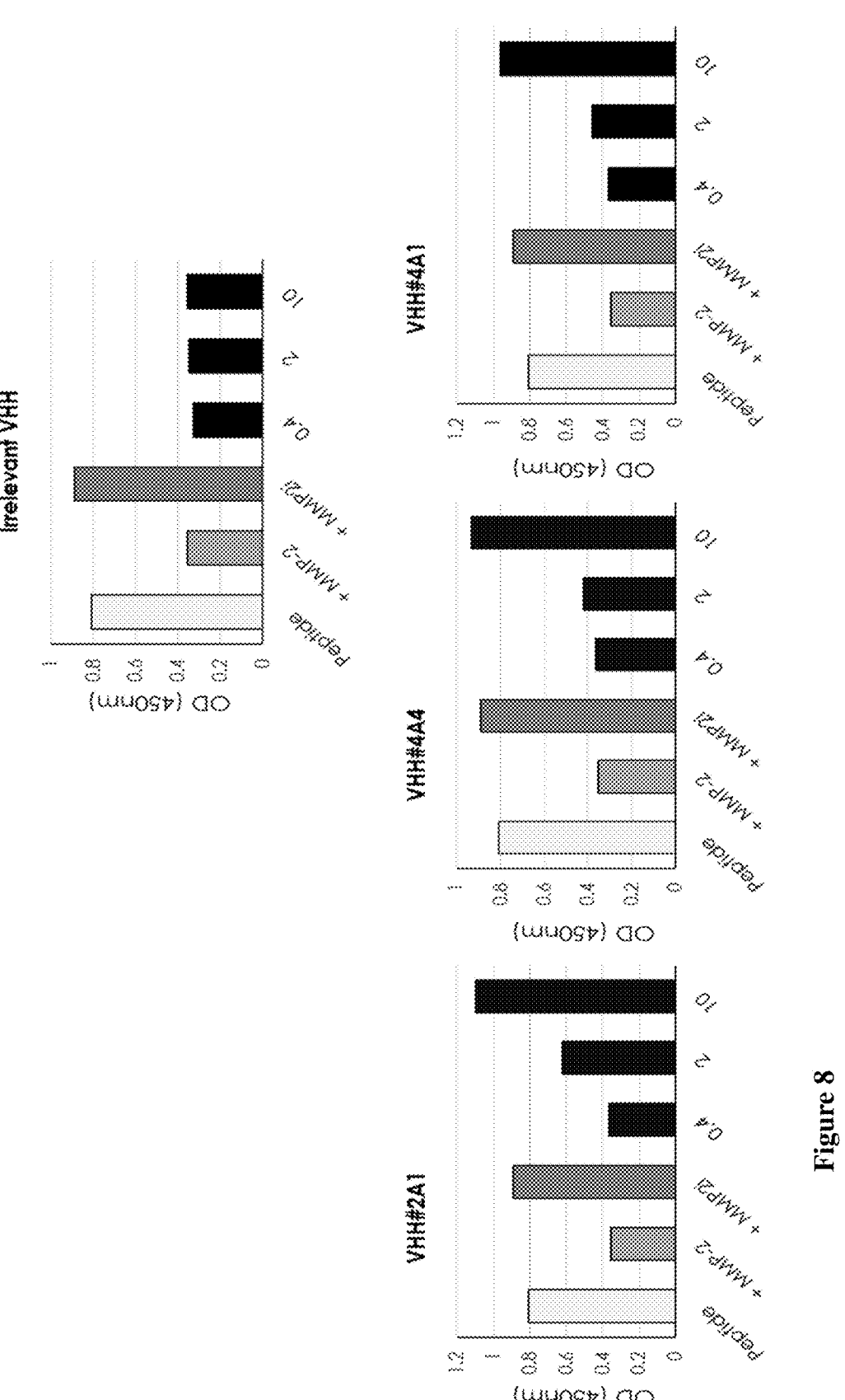
FIG. 8: In-vitro blocking of the MMP-2-mediated cleavage of human CD28 stalk region by VHH clones. A c-Myc conjugated and biotinylated human CD28 stalk region dimeric peptide (1 µM) was incubated with 50 ng rhMMP-2 in the presence of an MMP-2 inhibitor (TMI-1, 50 nM), or indicated VHH clones at various concentrations (0.4-10 µg/mL) for 5 hours. The mixtures were loaded on neutravidin coated ELISA maxi-sorb plates followed by extensive wash and detection of intact peptide by anti-cMyc HRP-conjugated antibody and development was carried out with TMB.
Figure 9:
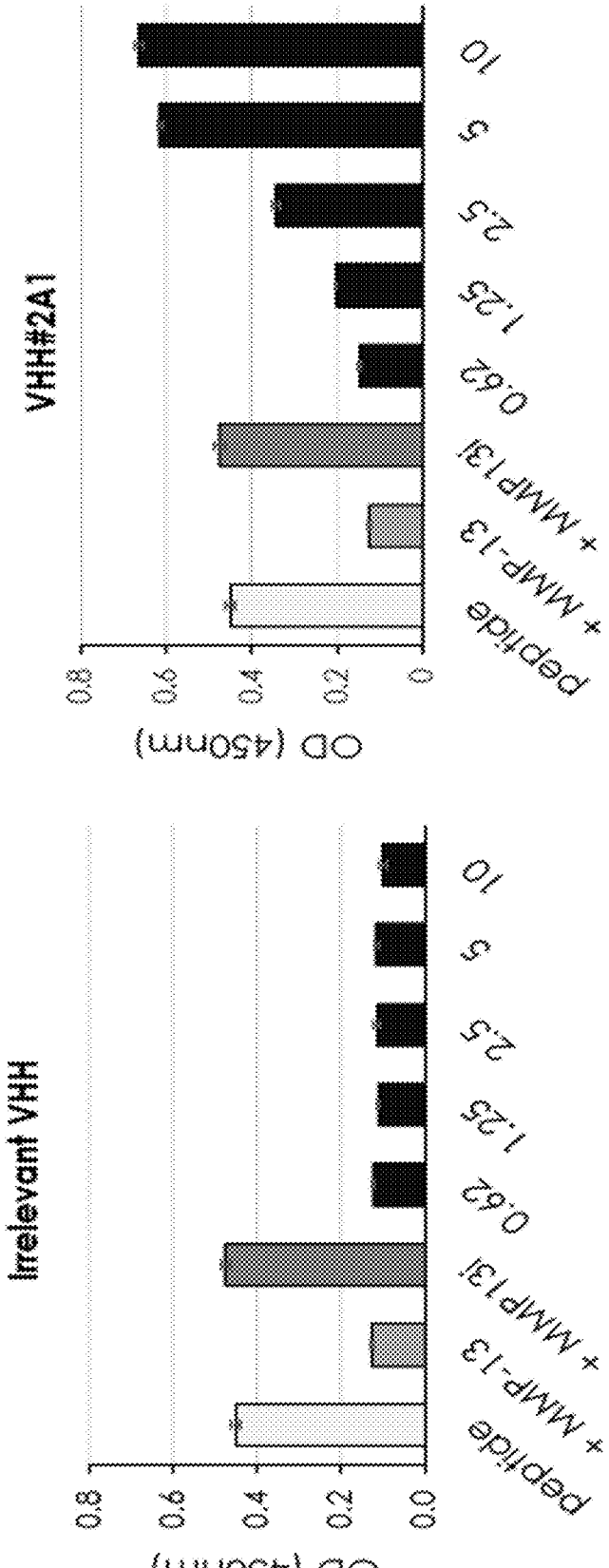
FIG. 9: In-vitro blocking activity of VHH clone 2A1 for the cleavage of human CD28 stalk region by MMP-13. A c-Myc and a biotinylated human CD28 stalk region dimeric peptide (1 µM) was incubated with 50 ng rhMMP-13 (light grey bar) in the presence of MMPi (TMI-1, 50 nM, dark grey bars), an irrelevant VHH clone (black bars in left chart), or VHH clone 2A1 (black bars in right chart) at various concentrations (0.62-10 µg/mL) for 5 hours. The mixtures were loaded on neutravidin coated ELISA maxi-sorb plates followed by extensive wash and detection of intact peptide by anti cMyc-HRP conjugated antibody and development was carried out with TMB.
Figure 10:
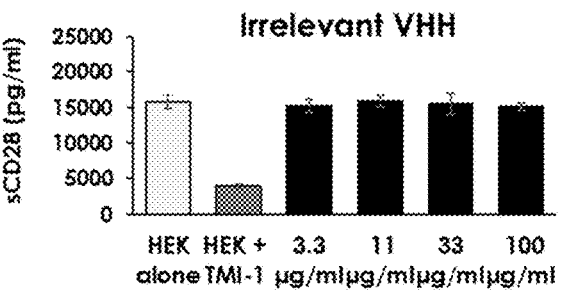
FIG. 10: Anti-CD28 stalk region VHH clones 2A1 and 4A4 inhibit CD28 shedding in HEK cells overexpressing human CD28. Levels of soluble CD28 were measured in culture media of HEK cells stably expressing human CD28 after 48 hr incubation. The effect of different treatments of MMP inhibitor (TMI-1, 1 dark grey bars), negative control of irrelevant VHH (top left chart, black bars) or anti-CD28 stalk region VHH clones (black bars) at various concentrations (3.3-100 µg/mL) on the level of soluble CD28 is depicted. The levels of soluble human CD28 in the supernatant were quantified with standardized sandwich ELISA (R&D system).
Figure 10:
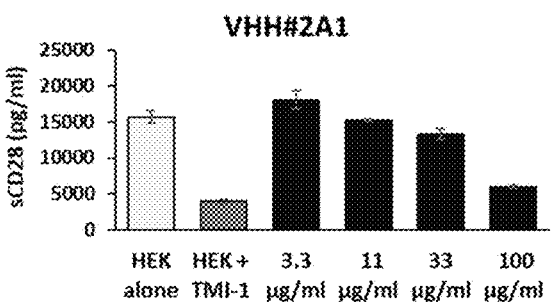
Figure 10:
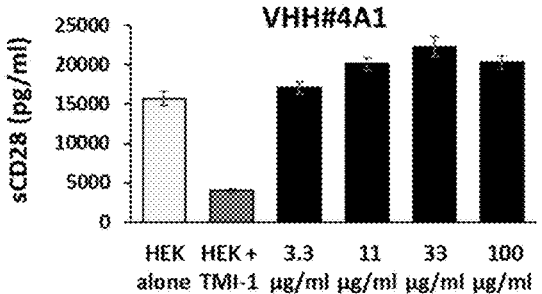
Figure 10:
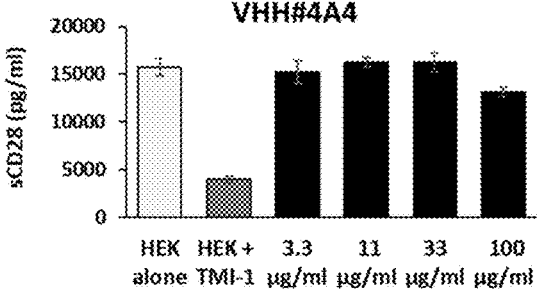
Figure 11:
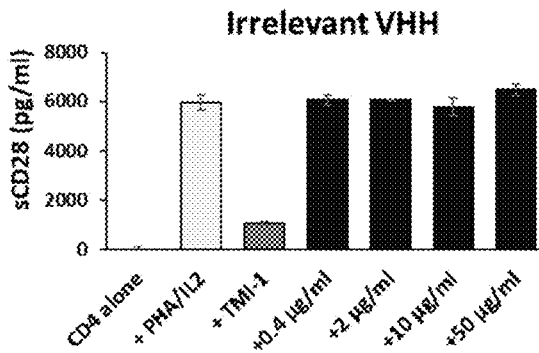
FIG. 11: Anti-CD28 stalk region VHH clones 2A1 and 4A4 inhibit CD28 shedding in isolated CD4 T cells activated by PHA and IL2. Levels of soluble CD28 were measured in culture media of isolated human CD4 T cells stimulated with 5 µg/mL PHA and 200 IU/mL IL-2 (light grey bar). The effect of different treatments of MMP inhibitor (TMI-1, 1 dark grey bars), negative control of irrelevant VHH (top left chart, black bars), anti-CD28 stalk region VHH clones or Fab format of antibody M9 clone (black bars) at various concentrations (0.4-50 µg/mL) on amount of soluble CD28 is depicted. The levels of soluble human CD28 in the supernatant were quantified with standardized sandwich ELISA (R&D system).
Figure 11:
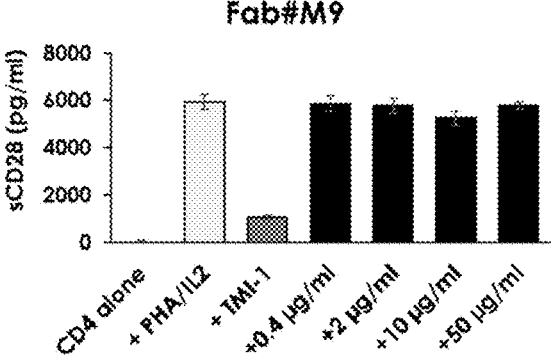
Figure 11:
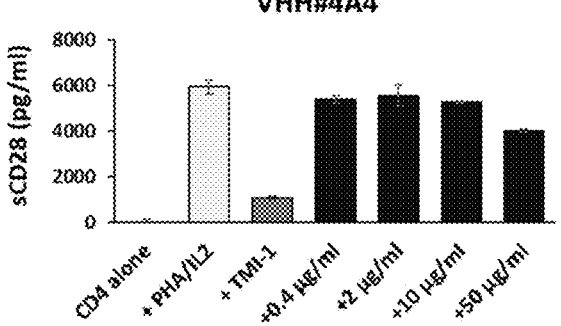
Figure 11:
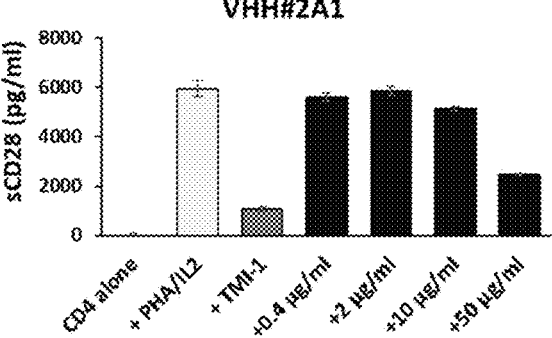
Figure 12:
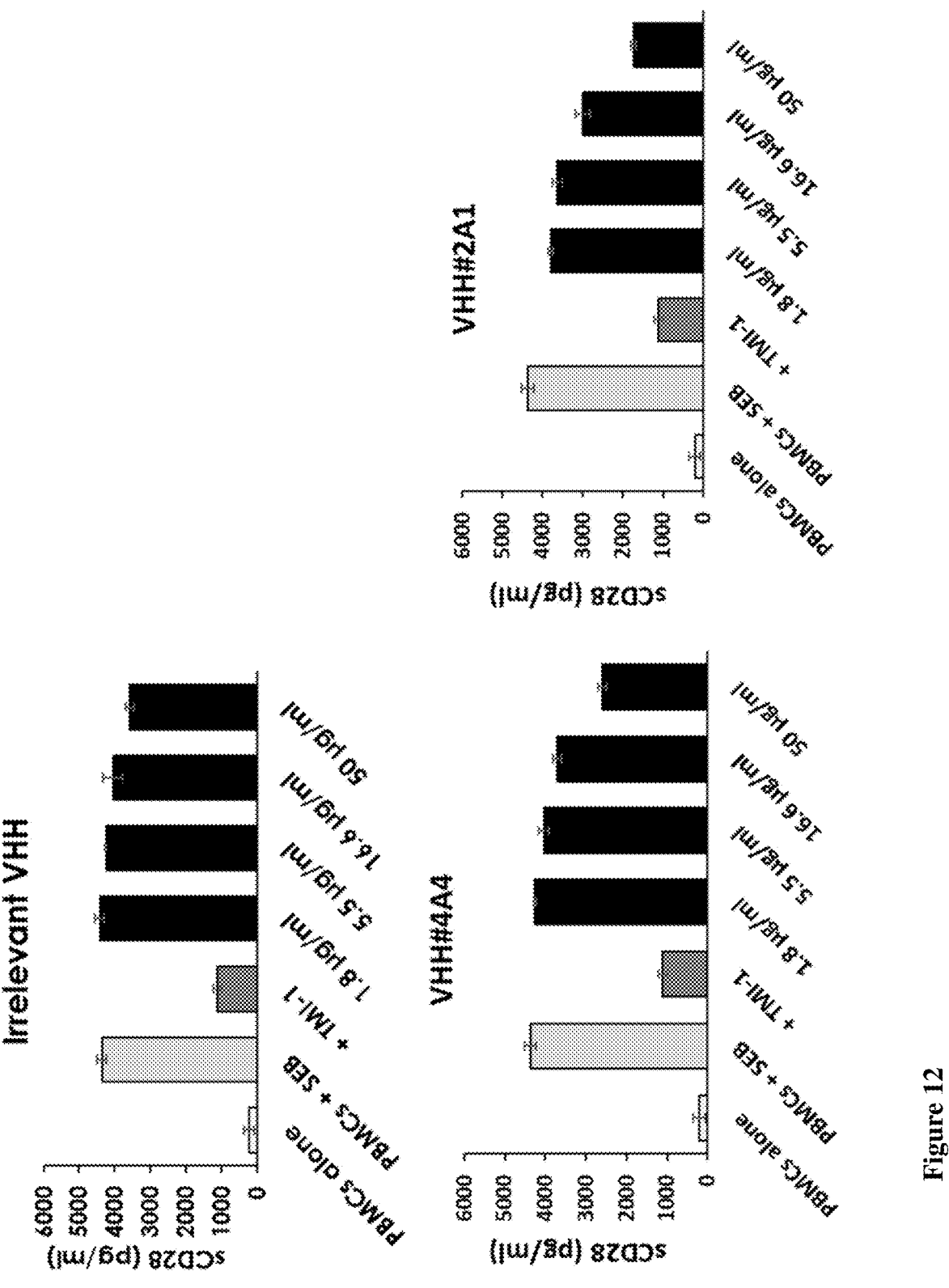
FIG. 12: Anti-CD28 stalk region VHH clones 2A1 and 4A4 inhibit CD28 shedding in PBMC activated by super-antigen. Levels of soluble CD28 were measured in culture media of isolated PBMC stimulated with 1 ng/mL SEB (light grey bar). The effect of different treatments of MMP inhibitor (TMI-1, 1 dark grey bars), negative control of irrelevant VHH (top left chart, black bars), anti-CD28 stalk region VHH clones (black bars) at various concentrations (0.4-50 µg/mL) on amount of soluble CD28 is depicted. The levels of soluble human CD28 in the supernatant were quantified with standardized sandwich ELISA (R&D system).

Anti-shedding activity was confirmed both on the peptide and the cellular level. ELISA techniques were used to detect intact human CD28 stalk region dimeric peptide to confirm that the VHH clones block the cleavage of human CD28 stalk region by MMP-2 (FIG. 8), and MMP-13 (FIG. 9). On the cellular level, standard sandwich ELISA was used to confirm the efficacy of the VHH clones in inhibiting sCD28 shedding by measuring the levels of human sCD28 in the supernatant of HEK cells overexpressing human CD28 (FIG. 10), isolated CD4 T cells activated by PHA and IL-2 (FIG. 11) and PBMC activated by a superantigen (FIG. 12).

35

36

Figure 13:
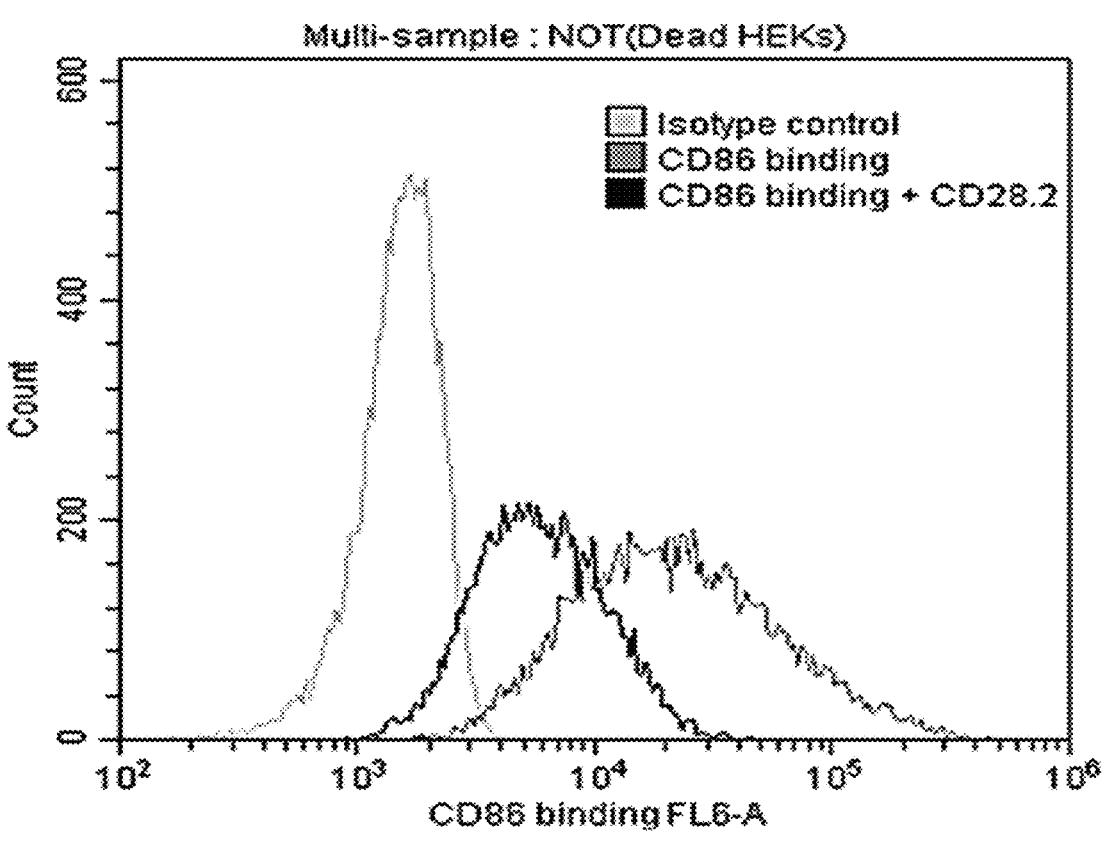
FIG. 13: Anti CD28 stalk region VHH clones do not block ligand binding to membranal CD28. HEK293 cells over expressing human CD28 were monitored by flow-cytometry for CD86-Fc (2 µg/mL) binding using secondary anti human Fc antibody conjugated to AlexaFlour 647. Addition of anti CD28 VHH clones to CD86-Fc (30 µg/mL, black histogram) did not change the magnitude of CD86 binding while addition of commercial antibody clone CD28.2 (10 µg/mL, upper left chart, black histogram) diminished binding significantly.
Figure 13:
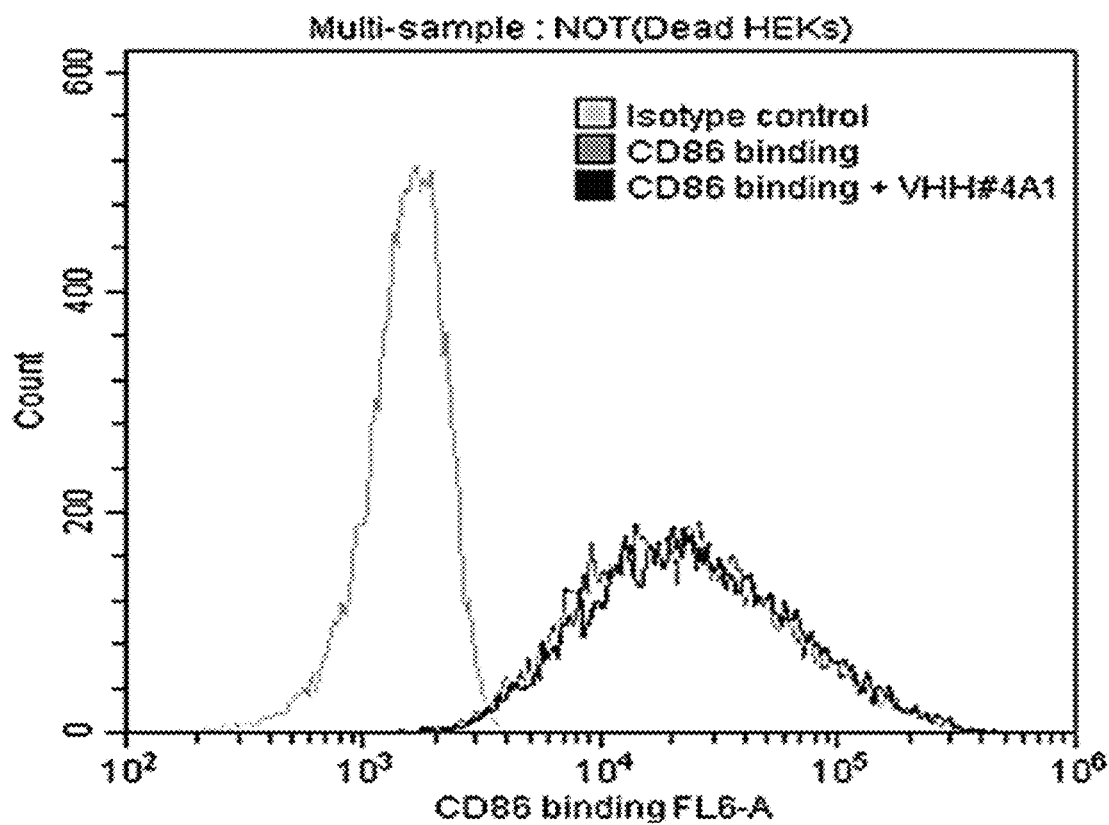
Figure 13:
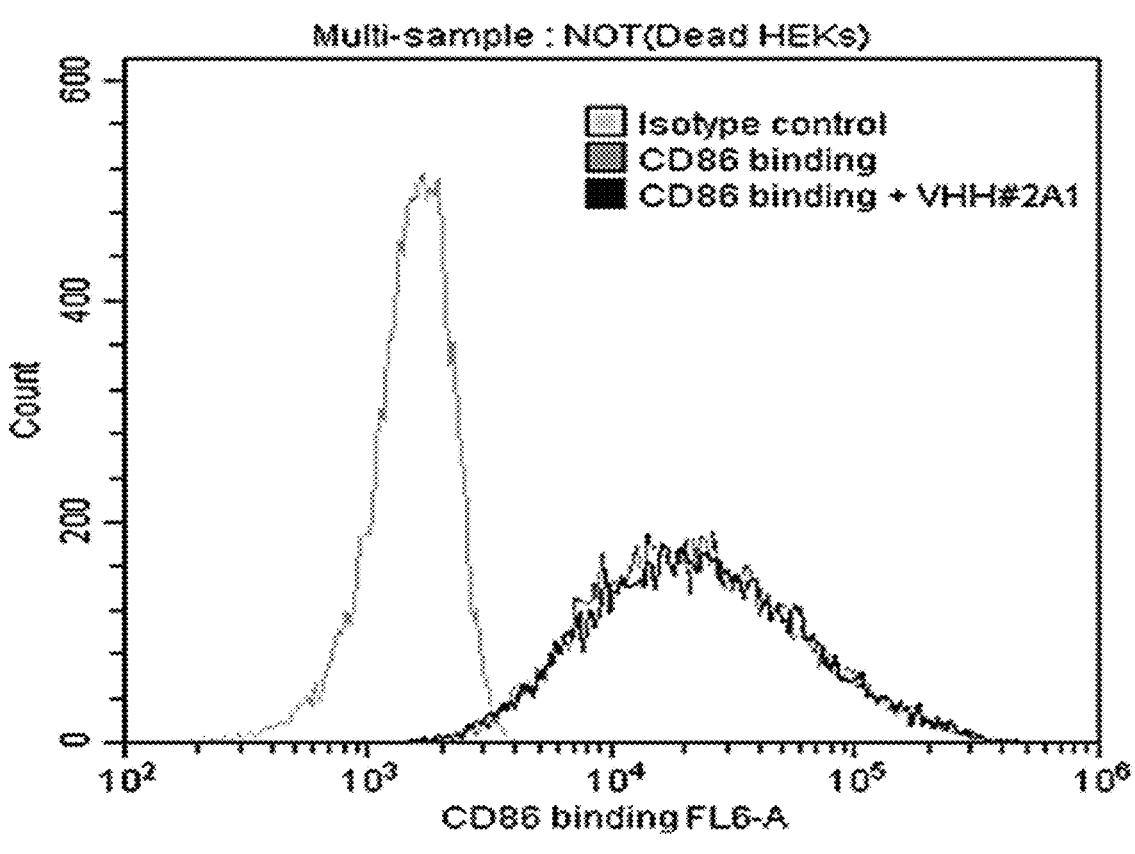
Figure 13:
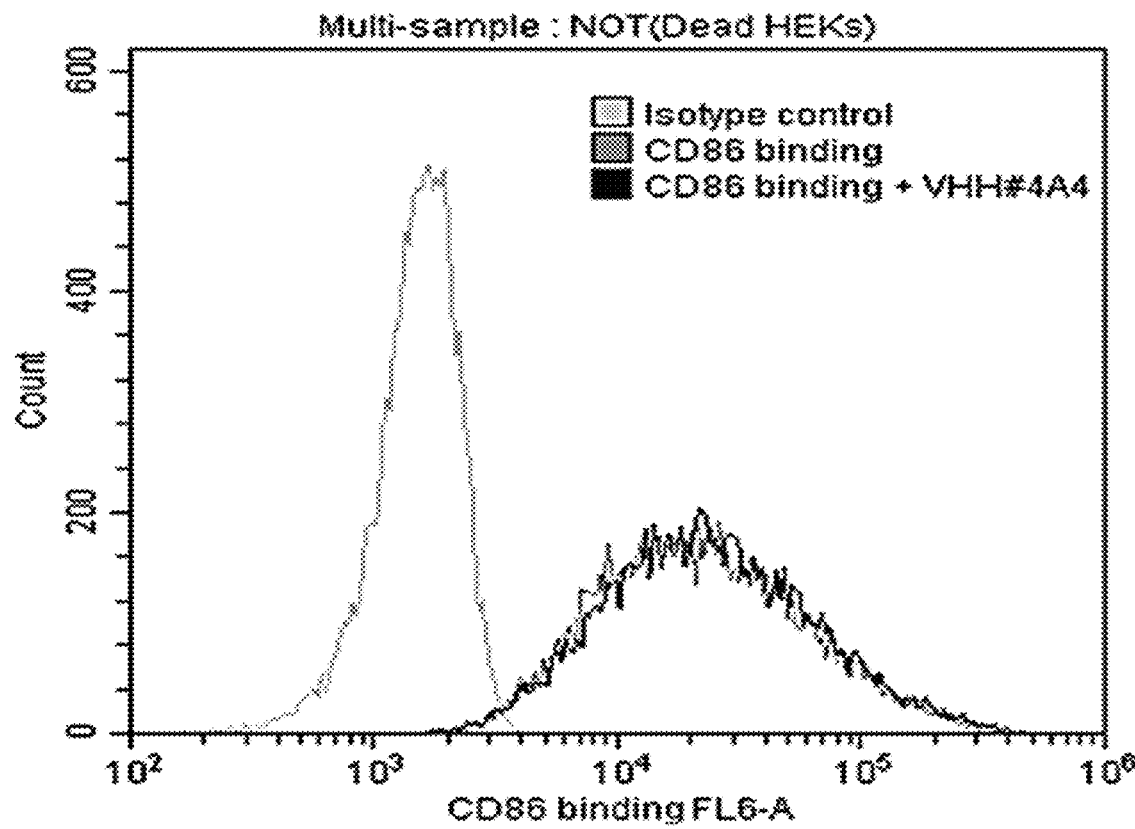
Figure 14:
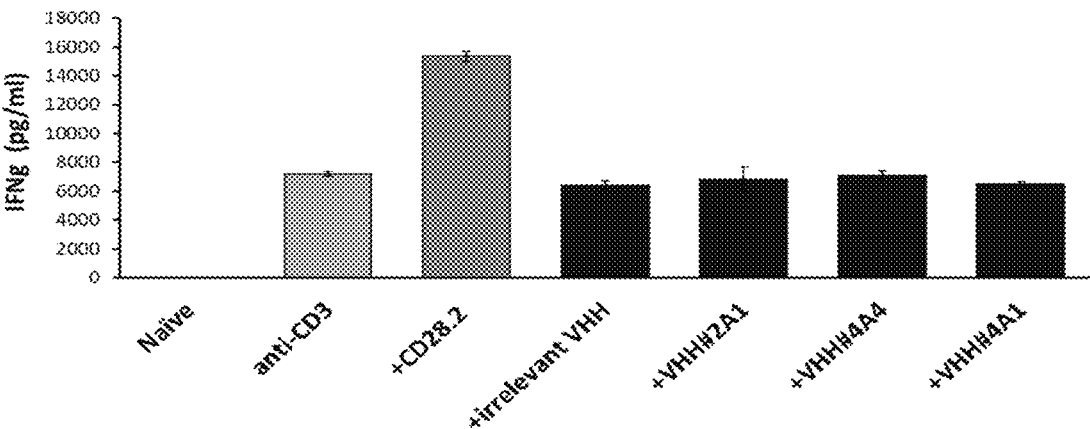
FIG. 14: Agonist effect evaluation of anti-CD28 VHH clones. Human isolated CD3 cells were stimulated for 2 days with plate bound anti-CD3 (OKT3, 2 µg/mL, light grey bar) in the presence of anti-CD28 agonist antibody clone 28.2 (2 µg/mL, dark grey bar) serving as positive control, anti-CD28 stalk region VHHs or an irrelevant VHH clone (20 µg/mL, black bars). The concentration of human IFN gamma secreted into the supernatant was quantified with standardized sandwich ELISA (Biolegend).
Figure 15:
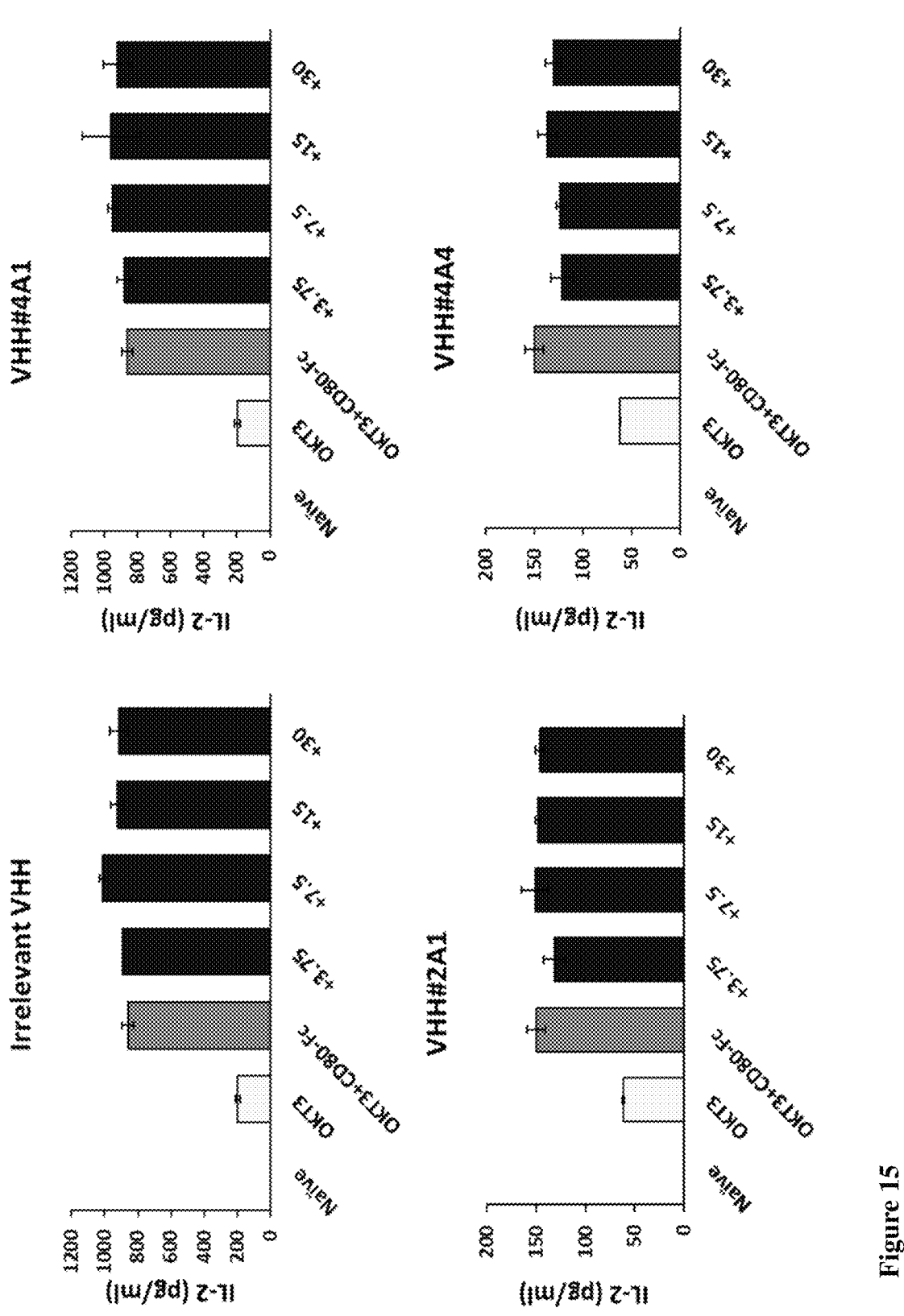
FIG. 15: Antagonist effect evaluation of anti-CD28 VHH clones. Human isolated CD3 cells were stimulated for 24 hours with plate bound anti-CD3 (OKT3, 2 µg/mL, light grey bar) in the presence of recombinant CD80-Fc protein (5 µg/mL, dark grey bar) serving as ligand for CD28 co-stimulation. An irrelevant VHH clone (top left chart) or the anti-CD28 stalk region VHHs were added at various concentrations (3.75-30 µg/mL, black bars). The concentration of human IL-2 in the supernatant was quantified with standardized sandwich ELISA (Biolegend).

Critically, the VHH clones were found to not impair human CD28 functionality. Using flow-cytometry, it was found that the VHH clones do not change the magnitude of CD86 binding to membrane CD28 (FIG. 13.). Standard sandwich ELISA was used to show the VHH clones do not agonize CD28 as measured by the secreted levels of the inflammatory cytokine interferon gamma (FIG. 14). Activating antibody CD28.2 was used as a positive control. Similarly, standard sandwich ELISA was used to show that the VHH clones do not antagonize CD80-Fc stimulation through CD28, as measured by the secreted levels of the cytokine IL-2 (FIG. 15).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for producing an agent for decreasing soluble CD28 (sCD28) levels, treating cancer, or improving PD-1 and/or PD-L1 based immunotherapy, the method comprising:

- screening agents for their ability to bind to a CD28 extracellular domain or fragment thereof and selecting at least one agent that binds, testing an ability of said at least one selected agent to block cleavage of membranal CD28 (mCD28) by MMP-2, MMP-13 or both by at least one assay, and selecting at least one agent that blocks cleavage of mCD28 by MMP-2, MMP-13 or both; or

- culturing a host cell comprising one or more vectors comprising a nucleic acid sequence encoding an agent, wherein the nucleic acid sequence is that of an agent that was selected by:
  - i. screening agents for their ability to that bind to a CD28 extracellular domain or fragment thereof and selecting at least one agent that binds;
  - ii. testing an ability of said at least one selected agent to block cleavage of mCD28 by MMP-2, MMP-13 or both; and
  - iii. selecting at least one agent that blocks cleavage of mCD28 by MMP-2, MMP-13 or both;

- wherein said agent is selected from an antibody, a Fab fragment, a single chain antibody, a DARPin and a single domain antibody; and

- wherein said at least one assay comprises: contacting cells expressing said mCD28 with said agent in the presence of said MMP-2, MMP-13 or both and measuring sCD28 levels produced or uncleaved mCD28 levels on said cells, wherein a decrease is sCD28 levels or an increase in uncleaved mCD28 levels as compared to levels from/on cells in the presence of said MMP-2, MMP-13 or both in the absence of said agent indicates the agent blocks cleavage of mCD28 by MMP-2, MMP-13 or both;

- thereby producing an agent for decreasing soluble CD28 (sCD28) levels, treating cancer, or improving PD-1 and/or PD-L1 based immunotherapy.

2. The method of claim 1, wherein screening agents for their ability to bind to CD28 extracellular domain or a fragment thereof is any one of:
   - a. screening agents for their ability to bind specifically to a CD28 stalk domain;
   - b. screening agents for their ability to bind specifically to an MMP-2, MMP-13 or both cleavage site in a CD28 stalk domain; and
   - c. screening agents for their ability to bind specifically to PSPL (SEQ ID NO: 15) in a CD28 stalk domain.

3. The method of claim 1, further comprising assaying mCD28 downstream signaling in the presence of said obtained agent and selecting at least one agent that neither substantially agonizes nor substantially antagonizes mCD28 signaling.

4. The method of claim 1, comprising testing an ability of said agent to block cleavage of mCD28 by MMP-2, and selecting at least one agent that blocks cleavage of mCD28 by MMP-2, or culturing a host cell comprising one or more vectors comprising a nucleic acid sequence encoding an agent, wherein the nucleic acid sequence is that of an agent that was selected by a method comprising testing an ability of said agent to block cleavage of mCD28 by MMP-2, and selecting at least one agent that blocks cleavage of mCD28 by MMP-2.

5. The method of claim 1, comprising testing an ability of said agent to block cleavage of mCD28 by MMP-13, and selecting at least one agent that blocks cleavage of mCD28 by MMP-13, or culturing a host cell comprising one or more vectors comprising a nucleic acid sequence encoding an agent, wherein the nucleic acid sequence is that of an agent that was selected by a method comprising testing an ability of said agent to block cleavage of mCD28 by MMP-13, and selecting at least one agent that blocks cleavage of mCD28 by MMP-13.

6. The method of claim 1, wherein said agent is selected from a Fab fragment, a single chain antibody, a DARPin and a single domain antibody.

7. The method of claim 6, wherein said agent is a single domain antibody.

* * * * *

SEQUENCE LISTING

```
<160> NUMBER OF SEQ ID NOS: 31

<210> SEQ ID NO 1
<211> LENGTH: 220
<212> TYPE: PRT
<213> ORGANISM: Homo sapiens

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 2
<211> LENGTH: 202
<212> TYPE: PRT
<213> ORGANISM: Homo sapiens

<400> SEQUENCE: 2

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30
```

-continued

```
Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Tyr Leu Asp Asn Glu Lys Ser Asn Gly
                100                 105                 110

Thr Ile Ile His Val Lys Gly Lys His Leu Cys Pro Ser Pro Leu Phe
                115                 120                 125

Pro Gly Pro Ser Lys Pro Phe Trp Val Leu Val Val Val Gly Gly Val
        130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200
```

```
<210> SEQ ID NO 3
<211> LENGTH: 663
<212> TYPE: DNA
<213> ORGANISM: Homo sapiens

<400> SEQUENCE: 3
atgctcaggc tgctcttggc tctcaactta ttcccttcaa ttcaagtaac aggaaacaag      60
attttggtga agcagtcgcc catgcttgta gcgtacgaca atgcggtcaa ccttagctgc     120
aagtattcct acaatctctt ctcaagggag ttccgggcat cccttcacaa aggactggat     180
agtgctgtgg aagtctgtgt tgtatatggg aattactccc agcagcttca ggtttactca     240
aaaacggggt tcaactgtga tgggaaattg ggcaatgaat cagtgacatt ctacctccag     300
aatttgtatg ttaaccaaac agatatttac ttctgcaaaa ttgaagttat gtatcctcct     360
ccttacctag acaatgagaa gagcaatgga accattatcc atgtgaaagg aaaacacctt     420
tgtccaagtc ccctatttcc cggaccttct aagcccttt gggtgctggt ggtggttggt      480
ggagtcctgg cttgctatag cttgctagta acagtggcct ttattatttt ctgggtgagg     540
agtaagagga gcaggctcct gcacagtgac tacatgaaca tgactccccg ccgcccgggg     600
cccacccgca agcattacca gccctatgcc ccaccacgcg acttcgcagc ctatcgctcc     660
tga                                                                    663
```

```
<210> SEQ ID NO 4
<211> LENGTH: 27
<212> TYPE: PRT
<213> ORGANISM: Homo sapiens

<400> SEQUENCE: 4

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 5
<211> LENGTH: 144
<212> TYPE: PRT
<213> ORGANISM: Homo sapiens

<400> SEQUENCE: 5

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
            130                 135                 140

<210> SEQ ID NO 6
<211> LENGTH: 126
<212> TYPE: PRT
<213> ORGANISM: Homo sapiens

<400> SEQUENCE: 6

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
        50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
                100                 105                 110

Thr Ile Ile His Val Lys Gly Lys His Leu Cys Pro Ser Pro
            115                 120                 125

<210> SEQ ID NO 7
<211> LENGTH: 16
<212> TYPE: PRT
<213> ORGANISM: Homo sapiens

<400> SEQUENCE: 7

Gly Lys His Leu Cys Pro Ser Pro Leu Phe Pro Gly Pro Ser Lys Pro
1               5                   10                  15
```

```
<210> SEQ ID NO 8
<211> LENGTH: 15
<212> TYPE: PRT
<213> ORGANISM: Homo sapiens

<400> SEQUENCE: 8

Lys Gly Lys His Leu Cys Pro Ser Pro Leu Phe Pro Gly Pro Ser
1               5                   10                  15

<210> SEQ ID NO 9
<211> LENGTH: 17
<212> TYPE: PRT
<213> ORGANISM: Homo sapiens

<400> SEQUENCE: 9

Lys Gly Lys His Leu Cys Pro Ser Pro Leu Phe Pro Gly Pro Ser Lys
1               5                   10                  15

Pro

<210> SEQ ID NO 10
<211> LENGTH: 19
<212> TYPE: PRT
<213> ORGANISM: Homo sapiens

<400> SEQUENCE: 10

His Val Lys Gly Lys His Leu Cys Pro Ser Pro Leu Phe Pro Gly Pro
1               5                   10                  15

Ser Lys Pro

<210> SEQ ID NO 11
<211> LENGTH: 134
<212> TYPE: PRT
<213> ORGANISM: Homo sapiens

<400> SEQUENCE: 11

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
            115                 120                 125

Pro Gly Pro Ser Lys Pro
        130

<210> SEQ ID NO 12
<211> LENGTH: 9
<212> TYPE: PRT
<213> ORGANISM: Homo sapiens

<400> SEQUENCE: 12
```

-continued

```
Lys Gly Lys His Leu Ser Pro Ser Pro
1               5

<210> SEQ ID NO 13
<211> LENGTH: 9
<212> TYPE: PRT
<213> ORGANISM: Homo sapiens

<400> SEQUENCE: 13

Leu Phe Pro Gly Pro Ser Lys Pro Glu
1               5

<210> SEQ ID NO 14
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: X1
<222> LOCATION: (2)..(2)
<223> OTHER INFORMATION: X1 is any amino acid
<220> FEATURE:
<221> NAME/KEY: X2
<222> LOCATION: (3)..(3)
<223> OTHER INFORMATION: X2 is any amino acid
<220> FEATURE:
<221> NAME/KEY: X3
<222> LOCATION: (4)..(4)
<223> OTHER INFORMATION: X3 is any hydrophobic amino acid

<400> SEQUENCE: 14

Pro Xaa Xaa Xaa
1

<210> SEQ ID NO 15
<211> LENGTH: 4
<212> TYPE: PRT
<213> ORGANISM: Homo sapiens

<400> SEQUENCE: 15

Pro Ser Pro Leu
1

<210> SEQ ID NO 16
<211> LENGTH: 18
<212> TYPE: PRT
<213> ORGANISM: Artificial
<220> FEATURE:
<223> OTHER INFORMATION: Synthetic

<400> SEQUENCE: 16

Lys Gly Lys His Leu Ser Pro Ser Pro Leu Phe Pro Gly Pro Ser Lys
1               5                   10                  15

Pro Glu

<210> SEQ ID NO 17
<211> LENGTH: 33
<212> TYPE: PRT
<213> ORGANISM: Artificial
<220> FEATURE:
<223> OTHER INFORMATION: Synthetic

<400> SEQUENCE: 17

Glu Gln Lys Leu Ile Ser Glu Glu Asp Leu Gly Gly Gly Gly His Val
1               5                   10                  15
```

```
Lys Gly Lys His Leu Cys Pro Ser Pro Leu Phe Pro Gly Pro Ser Lys
            20                  25                  30

Pro

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Glu Gln Lys Leu Ile Ser Glu Glu Asp Leu
1               5                   10

<210> SEQ ID NO 19
<211> LENGTH: 33
<212> TYPE: PRT
<213> ORGANISM: Artificial
<220> FEATURE:
<223> OTHER INFORMATION: Synthetic

<400> SEQUENCE: 19

Glu Gln Lys Leu Ile Ser Glu Glu Asp Leu Gly Gly Gly Gly His Val
1               5                   10                  15

Lys Gly Lys His Leu Cys Pro Ser Pro Lys Phe Pro Gly Pro Ser Lys
            20                  25                  30

Pro

<210> SEQ ID NO 20
<211> LENGTH: 4
<212> TYPE: PRT
<213> ORGANISM: Artificial
<220> FEATURE:
<223> OTHER INFORMATION: Synthetic

<400> SEQUENCE: 20

Pro Ser Pro Lys
1

<210> SEQ ID NO 21
<211> LENGTH: 5
<212> TYPE: PRT
<213> ORGANISM: Artificial
<220> FEATURE:
<223> OTHER INFORMATION: Synthetic

<400> SEQUENCE: 21

Ile Asn Ala Met Gly
1               5

<210> SEQ ID NO 22
<211> LENGTH: 16
<212> TYPE: PRT
<213> ORGANISM: Artificial
<220> FEATURE:
<223> OTHER INFORMATION: Synthetic

<400> SEQUENCE: 22

Ala Ile Ser Gly Gly Gly Asp Thr Tyr Tyr Ala Asp Ser Val Lys Gly
1               5                   10                  15

<210> SEQ ID NO 23
<211> LENGTH: 9
<212> TYPE: PRT
```

```
<213> ORGANISM: Artificial
<220> FEATURE:
<223> OTHER INFORMATION: Synthetic

<400> SEQUENCE: 23

Asp Leu Tyr Gly Ser Asp Tyr Trp Asp
1               5

<210> SEQ ID NO 24
<211> LENGTH: 5
<212> TYPE: PRT
<213> ORGANISM: Artificial
<220> FEATURE:
<223> OTHER INFORMATION: Synthetic

<400> SEQUENCE: 24

Ile Asn Ala Met Ala
1               5

<210> SEQ ID NO 25
<211> LENGTH: 16
<212> TYPE: PRT
<213> ORGANISM: Artificial
<220> FEATURE:
<223> OTHER INFORMATION: Synthetic

<400> SEQUENCE: 25

Ala Ile Thr Ser Ser Gly Ser Thr Asn Tyr Ala Asn Ser Val Lys Gly
1               5                   10                  15

<210> SEQ ID NO 26
<211> LENGTH: 9
<212> TYPE: PRT
<213> ORGANISM: Artificial
<220> FEATURE:
<223> OTHER INFORMATION: Synthetic

<400> SEQUENCE: 26

Asp Glu Tyr Gly Ser Asp Tyr Trp Ile
1               5

<210> SEQ ID NO 27
<211> LENGTH: 16
<212> TYPE: PRT
<213> ORGANISM: Artificial
<220> FEATURE:
<223> OTHER INFORMATION: Synthetic

<400> SEQUENCE: 27

Ala Ile Thr Ser Gly Gly Ser Thr Asn Tyr Ala Asp Ser Val Lys Gly
1               5                   10                  15

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Asp Leu Tyr Gly Glu Asp Tyr Trp Ile
1               5

<210> SEQ ID NO 29
<211> LENGTH: 126
<212> TYPE: PRT
<213> ORGANISM: Artificial
```

```
<220> FEATURE:
<223> OTHER INFORMATION: Synthetic

<400> SEQUENCE: 29

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
        35                  40                  45

Ala Ala Ile Ser Gly Gly Gly Asp Thr Tyr Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser Ala Ala Ala His His His His His His
        115                 120                 125

<210> SEQ ID NO 30
<211> LENGTH: 126
<212> TYPE: PRT
<213> ORGANISM: Artificial
<220> FEATURE:
<223> OTHER INFORMATION: Synthetic

<400> SEQUENCE: 30

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Leu Phe Ser Ile Asn
            20                  25                  30

Ala Met Ala Trp Tyr Arg Gln Ala Pro Gly Lys Gln Arg Glu Leu Val
        35                  40                  45

Ala Ala Ile Thr Ser Ser Gly Ser Thr Asn Tyr Ala Asn Ser Val Lys
    50                  55                  60

Gly Arg Phe Thr Val Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Val
                85                  90                  95

Val Asp Glu Tyr Gly Ser Asp Tyr Trp Ile Trp Gly Gln Gly Thr Gln
            100                 105                 110

Val Thr Val Ser Ser Ala Ala Ala His His His His His His
        115                 120                 125

<210> SEQ ID NO 31
<211> LENGTH: 126
<212> TYPE: PRT
<213> ORGANISM: Artificial
<220> FEATURE:
<223> OTHER INFORMATION: Synthetic

<400> SEQUENCE: 31

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30
```

-continued

```
Ala Met Gly Trp Tyr Arg Gln Ala Pro Gly Lys Gln Arg Glu Arg Val
        35              40              45

Ala Ala Ile Thr Ser Gly Gly Ser Thr Asn Tyr Ala Asp Ser Val Lys
    50              55              60

Gly Arg Phe Thr Ile Ser Arg Asp Asn Ala Lys Asn Thr Val Tyr Leu
65              70              75              80

Gln Met Asn Asn Leu Glu Pro Arg Asp Ala Gly Val Tyr Tyr Cys Val
                85              90              95

Val Asp Leu Tyr Gly Glu Asp Tyr Trp Ile Trp Gly Gln Gly Thr Gln
            100             105             110

Val Thr Val Ser Ser Ala Ala Ala His His His His His His
        115             120             125
```